United States Patent
Satchivi et al.

(10) Patent No.: US 10,219,513 B2
(45) Date of Patent: Mar. 5, 2019

(54) **SAFENING 4-AMINO-3-CHLORO-6-(4-CHLORO-2-FLUORO-3-METHOXYPHENYL)-5-FLUOROPYRIDINE-2-CARBOXYLIC ACID COMPOSITIONS IN *BRASSICA* SPECIES AND METHODS OF USE THEREOF**

(71) Applicant: Dow AgroSciences LLC, Indianapolis, IN (US)

(72) Inventors: Norbert M. Satchivi, Carmel, IN (US); Roger E. Gast, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/609,611

(22) Filed: May 31, 2017

(65) Prior Publication Data

US 2017/0354146 A1 Dec. 14, 2017

Related U.S. Application Data

(60) Provisional application No. 62/348,505, filed on Jun. 10, 2016.

(51) Int. Cl.
| | |
|---|---|
| *C07D 213/55* | (2006.01) |
| *A01N 43/40* | (2006.01) |
| *A01N 25/32* | (2006.01) |
| *C07C 25/13* | (2006.01) |
| *C07C 39/27* | (2006.01) |
| *C07C 43/225* | (2006.01) |
| *C07C 211/52* | (2006.01) |
| *C07C 217/84* | (2006.01) |
| *C07D 215/18* | (2006.01) |

(52) U.S. Cl.
CPC ............ *A01N 43/40* (2013.01); *A01N 25/32* (2013.01); *C07C 25/13* (2013.01); *C07C 39/27* (2013.01); *C07C 43/225* (2013.01); *C07C 211/52* (2013.01); *C07C 217/84* (2013.01); *C07D 213/55* (2013.01); *C07D 215/18* (2013.01)

(58) Field of Classification Search
None
See application file for complete search history.

(56) References Cited

U.S. PATENT DOCUMENTS

| | | | | |
|---|---|---|---|---|
| 7,314,849 | B2 * | 1/2008 | Balko | A01N 43/40 504/244 |
| 9,526,244 | B2 * | 12/2016 | Satchivi | A01N 43/54 |
| 2014/0031125 | A1 * | 1/2014 | Wells | G07F 17/32 463/40 |

OTHER PUBLICATIONS

Monsanto, http://www.monsantoglobal.com/global/au/products/documents/tech-topic-what-is-roundup-ready-canola.pdf What is Roundup Ready canola? pp. 1 and 2, obtained Oct. 22 (Year: 2018).*

Dow AgroSciences, http://msdssearch.dow.com/PublishedLiteratureDAS/dh_0314/0901b80380314b3b.pdf? What are Omega-9 Oils, Issue 3, pp. 1 and 2, August (Year: 2008).*

* cited by examiner

*Primary Examiner* — Zinna Northington Davis

(57) ABSTRACT

Provided herein are safened herbicidal compositions for use in *Brassica* species susceptible to injury by 4-amino-3-chloro-6-(4-chloro-2-fluoro-3-methoxyphenyl)-5-fluoropyridine-2-carboxylic acid comprising (a) a herbicidally effective amount of 4-amino-3-chloro-6-(4-chloro-2-fluoro-3-methoxyphenyl)-5-fluoropyridine-2-carboxylic acid or an agriculturally acceptable salt or ester of thereof, and (b) a safener. The safener can be a herbicide or a herbicide safener capable of safening the *Brassica* species susceptible to injury by 4-amino-3-chloro-6-(4-chloro-2-fluoro-3-methoxyphenyl)-5-fluoropyridine-2-carboxylic acid.

38 Claims, No Drawings

SAFENING 4-AMINO-3-CHLORO-6-(4-CHLORO-2-FLUORO-3-METHOXYPHENYL)-5-FLUOROPYRIDINE-2-CARBOXYLIC ACID COMPOSITIONS IN *BRASSICA* SPECIES AND METHODS OF USE THEREOF

This application claims a priority based on provisional application 62/348,505 which was filed in the U.S. Patent and Trademark Office on Jun. 10, 2016, the entire disclosure of which is hereby incorporated by reference.

BACKGROUND

The protection of *Brassica* species from weeds and other vegetation which inhibit the growth of the *Brassica* species is a constantly recurring problem. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. Such herbicides, however, can injure the *Brassica* species in addition to the weeds and other vegetation intended to be controlled.

SUMMARY

Provided herein are safened herbicidal compositions for use in *Brassica* species susceptible to injury by 4-amino-3-chloro-6-(4-chloro-2-fluoro-3-methoxyphenyl)-5-fluoropyridine-2-carboxylic acid. These safened herbicidal compositions contain (a) a herbicidally effective amount of 4-amino-3-chloro-6-(4-chloro-2-fluoro-3-methoxyphenyl)-5-fluoropyridine-2-carboxylic acid, an agriculturally acceptable salt or ester thereof, and (b) a safener. The safener can contain one or more herbicides capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species, a herbicide safener capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species, or mixtures thereof.

Also provided herein are methods for safening *Brassica* species susceptible to injury from 4-amino-3-chloro-6-(4-chloro-2-fluoro-3-methoxyphenyl)-5-fluoropyridine-2-carboxylic acid. These methods include applying to the *Brassica* species, contacting the vegetation, or area adjacent thereto with a herbicidal composition containing a herbicidally effective amount of 4-amino-3-chloro-6-(4-chloro-2-fluoro-3-methoxyphenyl)-5-fluoropyridine-2-carboxylic acid, an agriculturally acceptable salt or ester thereof, and (b) a safener. The safener can contain one or more herbicides capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species, a herbicide safener capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species, or mixtures thereof.

DETAILED DESCRIPTION

Surprisingly, it has been found that certain broadleaf herbicides, which are normally injurious to *Brassica* crops, can be made to cause reduced injury to the *Brassica* crops from 4-amino-3-chloro-6-(4-chloro-2-fluoro-3-methoxyphenyl)-5-fluoropyridine-2-carboxylic acid or an agriculturally acceptable salt or ester thereof while still providing excellent control of unwanted vegetation found in the *Brassica* crops. It has also been found that safeners that are traditionally used in monocot crops can reduce injury to dicot crops of 4-amino-3-chloro-6-(4-chloro-2-fluoro-3-methoxyphenyl)-5-fluoropyridine-2-carboxylic acid or an agriculturally acceptable salt or ester thereof while still providing excellent control of unwanted vegetation.

I. Definitions

As used herein, 4-amino-3-chloro-6-(4-chloro-2-fluoro-3-methoxyphenyl)-5-fluoropyridine-2-carboxylic acid has the following structure:

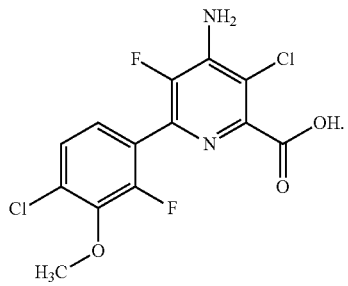 [SMILES: COc1c(Cl)ccc(-c2nc(C(=O)O)c(Cl)c(N)c2F)c1F]

4-Amino-3-chloro-6-(4-chloro-2-fluoro-3-methoxyphenyl)-5-fluoropyridine-2-carboxylic acid, also known as florpyrauxifen, has been described in U.S. Pat. No. 7,314,849 (B2), which is incorporated herein by reference in its entirety. Exemplary chemical forms of 4-amino-3-chloro-6-(4-chloro-2-fluoro-3-methoxyphenyl)-5-fluoropyridine-2-carboxylic acid include, but are not limited to, for example, benzyl 4-amino-3-chloro-6-(4-chloro-2-fluoro-3-methoxyphenyl)-5-fluoropyridine-2-carboxylate, which is also known as Rinskor™ active and florpyrauxifen-benzyl, and has the following structure:

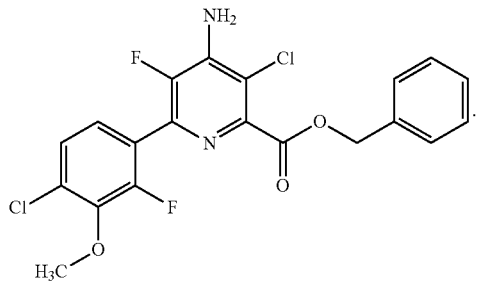 [SMILES: COc1c(Cl)ccc(-c2nc(C(=O)OCc3ccccc3)c(Cl)c(N)c2F)c1F]

Exemplary uses of 4-amino-3-chloro-6-(4-chloro-2-fluoro-3-methoxyphenyl)-5-fluoropyridine-2-carboxylic acid or an agriculturally acceptable salt or ester thereof include controlling undesirable vegetation, including grass, broadleaf and sedge weeds, in multiple non-crop and cropping situations.

As used herein, a herbicide capable of safening 4-amino-3-chloro-6-(4-chloro-2-fluoro-3-methoxyphenyl)-5-fluoropyridine-2-carboxylic acid, or an agriculturally acceptable salt or ester thereof, to the *Brassica* species includes clopyralid, quinclorac, picloram, or aminopyralid.

As used herein, clopyralid is 3,6-dichloro-2-pyridinecarboxylic acid, which has the following structure:

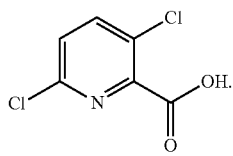 [SMILES: O=C(O)c1nc(Cl)ccc1Cl]

Exemplary uses of clopyralid include, but are not limited to, post-emergence control of many annual and perennial broadleaf weeds, e.g., in sugar beet, fodder beet, oilseed rape, maize, cereals, brassicas, onions, leeks, strawberries and flax, and in grassland and non-crop land. Exemplary chemical forms of clopyralid include, but are not limited to, for example, clopyralid MEA or clopyralid olamine, which is 2-hydroxyethanaminium 3,6-dichloro-2-pyridinecarboxylate and has the following structure:

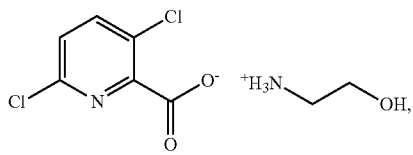

and clopyralid-triisopropanolammonium, which is (2RS, 2'RS,2"RS)-tris(2-hydroxypropyl)ammonium 3,6-dichloro-pyridine-2-carboxylate and has the following structure:

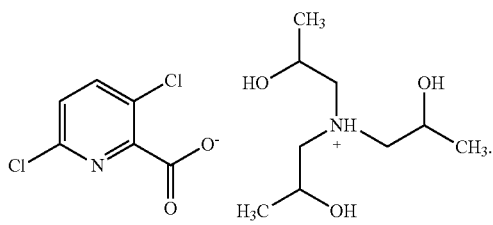

As used herein, quinclorac is 3,7-dichloro-8-quinolinecarboxylic acid, which has the following structure:

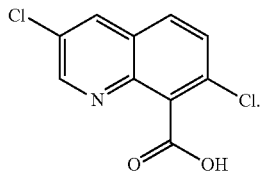 [SMILES: O=C(O)c1c(Cl)ccc2cc(Cl)cnc12]

Exemplary uses of quinclorac include, but are not limited to, pre- and post-emergence control of grass weeds (*Echinochloa* spp., *Aeschynomene* spp., *Sesbania* spp.) and other weeds in direct-seeded and transplanted rice.

As used herein, aminopyralid is 4-amino-3,6-dichloro-2-pyridinecarboxylic acid, which has the following structure:

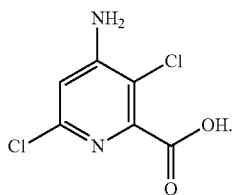 [SMILES: Nc1cc(Cl)nc(C(=O)O)c1Cl]

Exemplary uses of aminopyralid include, but are not limited to, its use for long-term control of annual and perennial broadleaf weeds, e.g., in range and pasture. Exemplary chemical forms of aminopyralid include, but are not limited to, for example, aminopyralid TIPA, which is tris (2-hydroxypropyl)ammonium 4-amino-3,6-dichloropyridine-2-carboxylate and has the following structure:

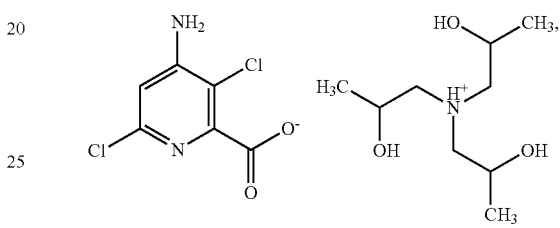

and aminopyralid-potassium, which is potassium 4-amino-3,6-dichloropyridine-2-carboxylate and has the following structure:

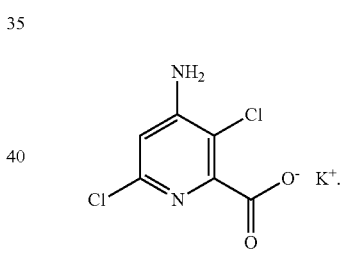

As used herein, picloram is 4-amino-3,5,6-trichloro-2-pyridinecarboxylic acid, which has the following structure:

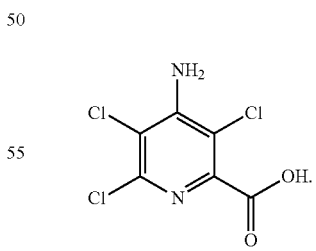

Exemplary uses of picloram include, but are not limited to, management of unwanted vegetation, e.g., in rangeland, grass pastures, forestry, as well as non-crop land and right-of-way sites. Exemplary chemical forms of picloram include, but are not limited to, for example, picloram $K^+$ salt, which is potassium 4-amino-3,5,6-trichloro-2-pyridinecarboxylate and has the following structure:

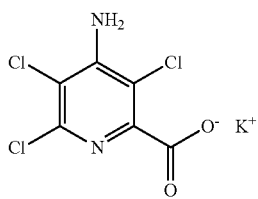 [SMILES: Nc1c(Cl)c(Cl)nc(C(=O)[O-])c1Cl ; [K+]]

As used herein, a herbicide safener capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species includes isoxadifen, cloquintocet, or mefenpyr.

As used herein, isoxadifen is 4,5-dihydro-5,5-diphenyl-1,2-oxazole-3-carboxylic acid, which has the following structure:

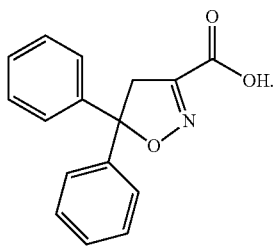 [SMILES: O=C(O)C1=NOC(c2ccccc2)(c2ccccc2)C1]

An exemplary form of isoxadifen is isoxadifen-ethyl or ethyl 4,5-dihydro-5,5-diphenyl-1,2-oxazole-3-carboxyalte, which the following structure:

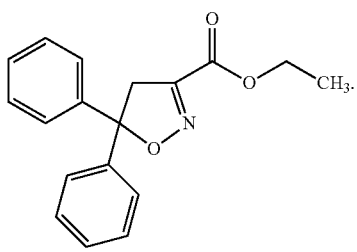 [SMILES: CCOC(=O)C1=NOC(c2ccccc2)(c2ccccc2)C1]

Isoxadifen-ethyl is used as a herbicide safener in maize and rice.

As used herein, safeners from the quinolinyloxyacetate family of chemicals are described in U.S. Pat. No. 4,902,340. Safeners from the quinolinyloxyacetate family of chemicals include derivatives of cloquintocet, such as cloquintocet acid, cloquintocet mexyl, cloquintocet triisopropylamine, and cloquintocet dimethylamine. Cloquintocet is (5-chloroquinolin-8-yloxy)acetate and has the following structure:

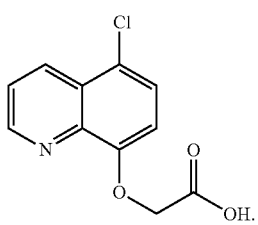 [SMILES: O=C(O)COc1ccc(Cl)c2cccnc12]

Cloquintocet mexyl is 1-methylhexyl (5-chloroquinolin-8-yloxy)acetate and has the following structure:

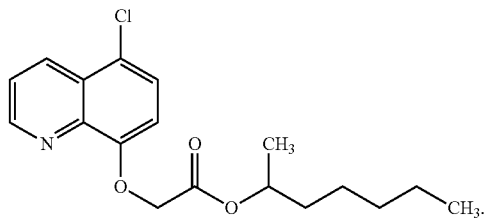 [SMILES: CCCCCC(C)OC(=O)COc1ccc(Cl)c2cccnc12]

Exemplary uses of cloquintocet mexyl include its use as a herbicide safener in combination with grass-active herbicides (pinoxaden, clodinafop-propargyl) for selective control of annual grasses (*Alopecurus myosuroides*, *Avena* spp., *Lolium* spp., *Phalaris* spp., *Poa trivialis*, *Setaria* spp.) in small grain cereals.

As used herein, mefenpyr is 1-(2,4-dichlorophenyl)-5-methyl-2-pyrazoline-3,5-dicarboxylic acid, which has the following structure:

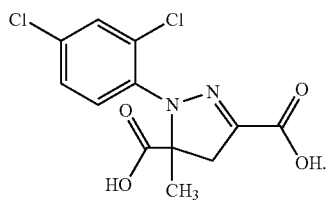 [SMILES: CC1(C(=O)O)CC(C(=O)O)=NN1c1ccc(Cl)cc1Cl]

An exemplary form of mefenpyr is mefenpyr-diethyl or diethyl (RS)-1-(2,4-dichlorophenyl)-5-methyl-2-pyrazoline-3,5-dicarboxylate, which has the following structure:

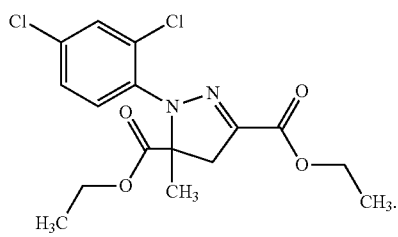 [SMILES: CCOC(=O)C1=NN(c2ccc(Cl)cc2Cl)C(C)(C(=O)OCC)C1]

Mefenpyr-diethyl is used as a herbicide safener in combination with fenoxaprop-P-ethyl, for selective weed control in wheat, rye, triticale and some barley varieties.

As used herein, herbicide means an active ingredient that kills, controls, or otherwise adversely modifies the growth of plants.

As used herein, a herbicide capable of safening refers to those herbicides or agriculturally acceptable salts or esters thereof when used to safen 4-amino-3-chloro-6-(4-chloro-2-fluoro-3-methoxyphenyl)-5-fluoropyridine-2-carboxylic acid or an agriculturally acceptable salt or ester thereof, to *Brassica* species, do not adversely impact the physical and/or biological properties of 4-amino-3-chloro-6-(4-chloro-2-fluoro-3-methoxyphenyl)-5-fluoropyridine-2-carboxylic acid or an agriculturally acceptable salt or ester thereof or compositions containing the same.

As used herein, a *Brassica* species susceptible to injury from 4-amino-3-chloro-6-(4-chloro-2-fluoro-3-methoxyphenyl)-5-fluoropyridine-2-carboxylic acid is a *Brassica* species that upon contact with 4-amino-3-chloro-6-(4-chloro-2-fluoro-3-methoxyphenyl)-5-fluoropyridine-2-carboxylic acid or an agriculturally acceptable salt or ester thereof experiences an adversely modifying effect such as, but not limited to, deviations from natural development, growth regulation, desiccation, growth retardation, plant death, and the like.

As used herein, plants and vegetation include, but are not limited to, dormant seeds, germinant seeds, emerging seedlings, plants emerging from vegetative propagules, immature vegetation, mature vegetation, reproductive vegetation and established vegetation.

As used herein, immature vegetation refers to small vegetative plants prior to reproductive stage, and mature vegetation refers to vegetative plants during and after reproductive stage.

*Brassica* species to be protected from the adverse effects of undesirable plant growth may be damaged to a certain degree when an effective dose of a herbicide is used. Safening, as used herein, means preventing or reducing the adverse effect of a herbicide on the *Brassica* species, i.e., protecting the *Brassica* species without, at the same time, noticeably influencing (i.e., overly diminishing) the herbicidal action on the undesirable plant growth, i.e., weeds, to be combated.

*Brassica* species susceptible to injury from 4-amino-3-chloro-6-(4-chloro-2-fluoro-3-methoxyphenyl)-5-fluoropyridine-2-carboxylic acid or an agriculturally acceptable salt or ester thereof include, but are not limited to, all varieties of canola and oilseed rape (*Brassica napus*, BRSNN), forage *brassica*, garden *brassica* and seed producing *brassica*, including spring rape or Spring Argentine canola (*Brassica napus*, BRSNS), winter oilseed rape (*Brassica napus*, BRSNW), Roundup Ready® canola (*Brassica napus*, RR-BRSNN), Nexera™ canola (*Brassica napus*, BRSNN-NEX), stem kale (*Brassica oleracea* var. *acephala* subvar. medullosa, BRSOM), Aparima Gold swede (*Brassica* sp., BRSSS), rutabaga (*Brassica napus* var. *napobrassica*, BRSNA), turnip or Polish canola (*Brassica rapa*, BRSRR), kale/Chinese kale (*Brassica alboglabra*, BRSAG), *Juncea* canola or brown mustard (*Brassica juncea*, BRSJU), broccoli/cauliflower (*Brassica oleracea* [botrytis], BRSOK), cabbage (*Brassica oleracea* [capitata], BRSOL), Abyssinian mustard (*Brassica carinata*, BRSCA), yellow mustard (*Sinapis alba*, SINAL) and Gold-of-Pleasure (*Camelina sativa*, CMASA).

As used herein, agriculturally acceptable salts and esters refer to salts and esters that exhibit herbicidal activity or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending upon the pH, may be in the dissociated or undissociated form. Exemplary salts include those derived from alkali or alkaline earth metals and those derived from ammonia and amines Exemplary cations include sodium, potassium, magnesium, and aminium cations of the formula:

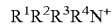

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment of the corresponding herbicidal carboxylic acid with a metal hydroxide, such as, for example, sodium hydroxide, with ammonia, with an amine, such as, for example, dimethylamine, trimethylamine, diethanolamine, 2-methyl-thiopropylamine, bisallylamine, 2-butoxyethylamine, morpholine, cyclododecylamine, or benzylamine or with a tetraalkylammonium hydroxide, such as, for example, tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, 2-octanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

II. Compositions

Provided herein are safened herbicidal compositions for use in *Brassica* species susceptible to injury by 4-amino-3-chloro-6-(4-chloro-2-fluoro-3-methoxyphenyl)-5-fluoropyridine-2-carboxylic acid containing: (a) a herbicidally effective amount of 4-amino-3-chloro-6-(4-chloro-2-fluoro-3-methoxyphenyl)-5-fluoropyridine-2-carboxylic acid or an agriculturally acceptable salt or ester thereof, or combinations thereof, and (b) a safener. The safener can be one or more herbicides capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species. The safener also can be a herbicide safener, capable of safening the 4-amino-3-chloro-6-(4-chloro-2-fluoro-3-methoxyphenyl)-5-fluoropyridine-2-carboxylic acid, or an agriculturally acceptable salt or ester thereof, or combinations to the *Brassica* species. Additionally, the safener can be a mixture of one or more herbicides capable of safening and one or more herbicide safeners. The described compositions may also contain an agriculturally acceptable adjuvant or carrier and additional inert ingredients.

As used herein, the herbicide capable of safening the 4-amino-3-chloro-6-(4-chloro-2-fluoro-3-methoxyphenyl)-5-fluoropyridine-2-carboxylic acid to the *Brassica* species may include one or more herbicides including, but not limited to, clopyralid, quinclorac, picloram, aminopyralid, or agriculturally acceptable salts or esters thereof, and combinations thereof.

In some embodiments, the compositions described herein may include 4-amino-3-chloro-6-(4-chloro-2-fluoro-3-methoxyphenyl)-5-fluoropyridine-2-carboxylic acid and clopyralid or an agriculturally acceptable salt or ester thereof. In some embodiments, the clopyralid is clopyralid (acid). In other embodiments, the clopyralid is clopyralid-olamine. In yet other embodiments, the clopyralid is clopyralid-triisopropanolammonium (TIPA).

In some embodiments, the compositions described herein may include 4-amino-3-chloro-6-(4-chloro-2-fluoro-3-methoxyphenyl)-5-fluoropyridine-2-carboxylic acid, clopyralid or an agriculturally acceptable salt or ester thereof, and a herbicide safener or an agriculturally acceptable salt or ester thereof. In some embodiments, the herbicide safener is isoxadifen-ethyl. In other embodiments, the herbicide safener is cloquintocet-mexyl. In yet other embodiments, the herbicide safener is mefenpyr-diethyl.

In some embodiments, the compositions described herein may include 4-amino-3-chloro-6-(4-chloro-2-fluoro-3-methoxyphenyl)-5-fluoropyridine-2-carboxylic acid and the quinclorac or an agriculturally acceptable salt or ester thereof. In some embodiments, the quinclorac is quinclorac (acid). In other embodiments, the quinclorac is quinclorac-dimethylammonium.

In some embodiments, the compositions described herein may include the use of 4-amino-3-chloro-6-(4-chloro-2-fluoro-3-methoxyphenyl)-5-fluoropyridine-2-carboxylic acid, quinclorac or an agriculturally acceptable salt or ester thereof, and a herbicide safener. In some embodiments, the herbicide safener is isoxadifen-ethyl. In other embodiments, the herbicide safener is cloquintocet-mexyl. In yet other embodiments, the herbicide safener is mefenpyr-diethyl.

In some embodiments, the compositions described herein may include 4-amino-3-chloro-6-(4-chloro-2-fluoro-3-methoxyphenyl)-5-fluoropyridine-2-carboxylic acid, clopyralid or an agriculturally acceptable salt or ester thereof, quinclorac or an agriculturally acceptable salt or ester thereof, and a herbicide safener. In some embodiments, the clopyralid is clopyralid (acid). In other embodiments, the clopyralid is clopyralid-olamine. In yet other embodiments, the clopyralid is clopyralid-triisopropanolammonium (TIPA). In some embodiments, the quinclorac is quinclorac (acid). In other embodiments, the quinclorac is quinclorac-dimethylammonium. In some embodiments, the herbicide safener is isoxadifen-ethyl. In other embodiments, the herbicide safener is cloquintocet-mexyl. In yet other embodiments, the herbicide safener is mefenpyr-diethyl.

In the compositions described herein, an agriculturally acceptable ester or salt of 4-amino-3-chloro-6-(4-chloro-2-fluoro-3-methoxyphenyl)-5-fluoropyridine-2-carboxylic acid is employed. An agriculturally acceptable ester, such as an arylalkyl or alkyl ester, can be employed. The ester can be a $C_1$-$C_4$ alkyl ester, a methyl ester, a n-butyl ester, a benzyl ester, or a substituted benzyl ester. Additionally, the carboxylic acid form or the carboxylate salt of the 4-amino-3-chloro-6-(4-chloro-2-fluoro-3-methoxyphenyl)-5-fluoropyridine-2-carboxylic acid may be used.

In the compositions described herein, the weight ratio of the 4-amino-3-chloro-6-(4-chloro-2-fluoro-3-methoxyphenyl)-5-fluoropyridine-2-carboxylic acid or a salt or ester thereof to the herbicide capable of safening the 4-amino-3-chloro-6-(4-chloro-2-fluoro-3-methoxyphenyl)-5-fluoropyridine-2-carboxylic acid to the *Brassica* species is within the range of from 1:300 to 1:1.2. The weight ratio of the 4-amino-3-chloro-6-(4-chloro-2-fluoro-3-methoxyphenyl)-5-fluoropyridine-2-carboxylic acid or a salt or ester thereof, to the herbicide capable of safening the 4-amino-3-chloro-6-(4-chloro-2-fluoro-3-methoxyphenyl)-5-fluoropyridine-2-carboxylic acid to the *Brassica* species can also be within the range from 1:290 to 1:1.2, 1:280 to 1:1.2, 1:270 to 1:1.2, 1:260 to 1:1.2, 1:250 to 1:1.2, 1:240 to 1:1.2, 1:220 to 1:1.2, 1:200 to 1:1.2, 1:180 to 1:1.2, 1:160 to 1:1.2, 1:140 to 1:1.2, 1:120 to 1:1.2, 1:100 to 1:1.2, 1:80 to 1:1.2, 1:300 to 1:2, 1:280 to 1:2, 1:260 to 1:2, 1:240 to 1:2, 1:220 to 1:2, 1:200 to 1:2, 1:180 to 1:2, 1:160 to 1:2, 1:140 to 1:2, 1:120 to 1:2, 1:100 to 1:2, 1:90 to 1:2, 1:80 to 1:2, 1:300 to 1:5, 1:280 to 1:5, 1:260 to 1:5, 1:240 to 1:5, 1:240 to 1:5, 1:220 to 1:5, 1:200 to 1:5, 1:180 to 1:5, 1:160 to 1:5, 1:120 to 1:5, 1:115 to 1:5, 1:110 to 1:5, 1:105 to 1:5, 1:100 to 1:5, 1:95 to 1:5, 1:90 to 1:5, 1:89 to 1:5, 1:88 to 1:5, 1:87 to 1:5, 1:86 to 1:5, 1:85 to 1:5, 1:84 to 1:5, 1:83 to 1:5, 1:82 to 1:5, or 1:80 to 1:5.

In the compositions described herein, the weight ratio of the 4-amino-3-chloro-6-(4-chloro-2-fluoro-3-methoxyphenyl)-5-fluoropyridine-2-carboxylic acid or a salt or ester thereof to a herbicide safener capable of safening the 4-amino-3-chloro-6-(4-chloro-2-fluoro-3-methoxyphenyl)-5-fluoropyridine-2-carboxylic acid to the *Brassica* species is within the range of from 1:50 to 10:1. The weight ratio of the 4-amino-3-chloro-6-(4-chloro-2-fluoro-3-methoxyphenyl)-5-fluoropyridine-2-carboxylic acid or a salt or ester thereof, to a herbicide safener capable of safening the 4-amino-3-chloro-6-(4-chloro-2-fluoro-3-methoxyphenyl)-5-fluoropyridine-2-carboxylic acid to the *Brassica* species can also be within the range from 1:45 to 10:1, 1:40 to 10:1, 1:35 to 10:1, 1:30 to 10:1, 1:25 to 10:1, 1:24 to 10:1, 1:23 to 10:1, 1:22 to 10:1, 1:20 to 10:1, 1:19 to 10:1, 1:18 to 10:1, 1:17 to 10:1, 1:16 to 10:1, 1:15 to 10:1, 1:10 to 10:1, 1:5 to 5:1, 1:2 to 2:1, 1:1.5 to 1.5:1, 1:1 to 1:2, 1:50 to 5:1, 1:48 to 5:1, 1:45 to 5:1, 1:40 to 5:1, 1:39 to 5:1, 1:38 to 5:1, 1:37 to 5:1, 1:36 to 5:1, 1:34 to 5:1, 1:32 to 5:1, 1:30 to 5:1, 1:30 to 5:1, 1:28 to 5:1, 1:26 to 5:1, 1:24 to 5:1, 1:20 to 5:1, 1:18 to 5:1, 1:16 to 5:1, 1:50 to 2:1, 1:48 to 2:1, 1:46 to 2:1, 1:44 to 2:1, 1:42 to 2:1, 1:40 to 2:1, 1:38 to 2:1, 1:36 to 2:1, 1:34 to 2:1, 1:34 to 2:1, 1:32 to 2:1, 1:30 to 2:1, 1:28 to 2:1, 1:26 to 2:1, 1:25 to 2:1, 1:24 to 2:1, 1:23 to 2:1, 1:22 to 2:1, 1:20 to 2:1, 1:19 to 2:1, 1:18 to 2:1, 1:17 to 2:1, or 1:16 to 2:1.

In certain embodiments of the compositions described herein, the 4-amino-3-chloro-6-(4-chloro-2-fluoro-3-methoxyphenyl)-5-fluoropyridine-2-carboxylic acid or a salt or ester thereof is used in combination with one or more of herbicides capable of safening the 4-amino-3-chloro-6-(4-chloro-2-fluoro-3-methoxyphenyl)-5-fluoropyridine-2-carboxylic acid to the *Brassica* species, or a salt or ester thereof, and one or more herbicide safeners, capable of safening the 4-amino-3-chloro-6-(4-chloro-2-fluoro-3-methoxyphenyl)-5-fluoropyridine-2-carboxylic acid to the *Brassica* species, or a salt or ester thereof. With regard to the compositions, in some embodiments, the three components are used in amounts such that the weight ratio of the (a) 4-amino-3-chloro-6-(4-chloro-2-fluoro-3-methoxyphenyl)-5-fluoropyridine-2-carboxylic acid or a salt or ester thereof is used in combination with (b) one or more of (i) herbicides capable of safening the 4-amino-3-chloro-6-(4-chloro-2-fluoro-3-methoxyphenyl)-5-fluoropyridine-2-carboxylic acid to the *Brassica* species, or a salt or ester thereof, and (ii) a herbicide safener, capable of safening the 4-amino-3-chloro-6-(4-chloro-2-fluoro-3-methoxyphenyl)-5-fluoropyridine-2-carboxylic acid to the *Brassica* species, or a salt or ester thereof [i.e. (a):(i):(ii)] is from about 1-25 of (a) to about 1.2-300 of (i) to about 1-50 of (ii). In additional embodiments, the weight ratios of the three components include from about 1-20 of (a) to about 1.2-250 of (i) to about 1-45 of (ii); from about 1-15 of (a) to about 1.2-200 of (i) to about 1-40 of (ii); from about 1-10 of (a) to about 1.2-150 of (i) to about 1-38 of (ii); from about 1-7.5 of (a) to about 1.2-140 of (i) to about 1-37 of (ii); from about 1-5 of (a) to about 2-200 of (i) to about 1-36 of (ii); from about 1-4.5 of (a) to about 1.2-100 of (i) to about 1-33 of (ii); from about 1-4 of (a) to about 1.2-80 of (i) to about 1-30 of (ii); from about 1-3.5 of (a) to about 3-180 of (i) to about 1-25 of (ii); and from about 1-3 of (a) to about 4-120 of (i) to about 1-20 of (c). In other embodiments, the weight ratio of the (a) 4-amino-3-chloro-6-(4-chloro-2-fluoro-3-methoxyphenyl)-5-fluoropyridine-2-carboxylic acid or a salt or ester thereof is used in combination with (b) one or more of (i) herbicides capable of safening the 4-amino-3-chloro-6-(4-chloro-2-fluoro-3-methoxyphenyl)-5-fluoropyridine-2-carboxylic acid to the *Brassica* species, or a salt or ester thereof, and (ii) a herbicide safener, capable of safening the 4-amino-3-chloro-6-(4-chloro-2-fluoro-3-methoxyphenyl)-5-fluoropyridine-2-carboxylic acid to the *Brassica* species, or a salt or ester thereof is within the range from about 1-2 of (a) to about 5-80 of (i) to about 1-16 of (ii).

Stated another way, the three components are used in amounts such that the weight ratio of the (a) 4-amino-3-chloro-6-(4-chloro-2-fluoro-3-methoxyphenyl)-5-fluoropyridine-2-carboxylic acid or a salt or ester thereof is used in combination with (b) one or more of (i) herbicides capable of safening the 4-amino-3-chloro-6-(4-chloro-2-fluoro-3-methoxyphenyl)-5-fluoropyridine-2-carboxylic acid to the *Brassica* species, or a salt or ester thereof, and (ii) a herbicide safener, capable of safening the 4-amino-3-chloro-6-(4-chloro-2-fluoro-3-methoxyphenyl)-5-fluoropyridine-2-carboxylic acid to the *Brassica* species, or a salt or ester thereof [i.e. (a):(i):(ii)] is from about 1:300:50 to about 10:120:1; from 1:30:50 to about 10:120:1; from about 1:200:36 to about 5:10:1; from about 1:32:36 to about 5:62.5:1; from about 1:80:16 to about 2:10:1; or from about 1:20:16 to about 2:40:1.

The safened compositions can further, be used in conjunction with 5-enolpyruvylshikimate-3-phosphate (EPSP) synthase inhibitors (e.g., glyphosate), glutamine synthetase inhibitors (e.g., glufosinate), synthetic auxins (e.g., dicamba, phenoxy auxins, pyridyloxy auxins), auxin transport inhibitors, acetyl CoA carboxylase (ACCase) inhibitors (e.g., aryloxyphenoxypropionates, cyclohexanediones, phenylpyrazolines), acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, and photosystem II inhibitors (e.g., triazines and bromoxynil).

The safened herbicide mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides, or applied sequentially with the other herbicide or herbicides. Some of the herbicides that can be employed in conjunction with the compositions and methods described herein include, but are not limited to: 4-CPA, 4-CPB, 4-CPP, 2,4-D, 3,4-DA, 2,4-DB, 3,4-DB, 2,4-DEB, 2,4-DEP, 3,4-DP, 2,3,6-TBA, 2,4,5-T, 2,4,5-TB, acetochlor, acifluorfen, aclonifen, alachlor, allidochlor, alloxydim, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bialaphos, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenquinotrione, fenteracol, fenthiaprop, fentrazamide, fenuron, flamprop, flamprop-M, flazasulfuron, florasulam, florpyrauxifen, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, fumiclorac, furyloxyfen, glufosinate salts and esters, glufosinate-ammonium, glufosinate-P-ammonium, glyphosate salts and esters, halauxifen, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lancotrione, lenacil, linuron, MAA, MAMA, MCPA, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, orbencarb, orthosulfamuron, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, SYN-523, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thifensulfuron-methyl, thiobencarb, tiafenacil, tiocarbazil, tioclorim, tolpyralate, topramezone, tralkoxydim, triafamone, tri-allate, triasulfuron, triaziflam, tribenuron, tribenuron-methyl, tricamba, triclopyr, tridiphane, trietazine, trifloxysulfuron, trifludimoxazin, trifluralin, triflusulfuron, trifop, trifopsime, trihydroxytriazine, trimeturon, tripropindan, tritac, tritosulfuron, vernolate, xylachlor and salts, esters, optically active isomers and mixtures thereof.

In some embodiments, the compositions described herein are employed in combination with one or more plant growth regulators, such as 2,3,5-tri-iodobenzoic acid, IAA, IBA, naphthaleneacetamide, α-naphthaleneacetic acids, benzyladenine, 4-hydroxyphenethyl alcohol, kinetin, zeatin, endothal, pentachlorophenol, thidiazuron, tribufos, aviglycine, ethephon, maleic hydrazide, gibberellins, gibberellic acid, abscisic acid, ancymidol, fosamine, glyphosine, isopyrimol, jasmonic acid, maleic hydrazide, mepiquat, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol, and trinexapac-ethyl. In some embodiments, the plant growth regulator is mixed with the 4-amino-3-chloro-6-(4-chloro-2-fluoro-3-methoxyphenyl)-5-fluoro-pyridine-2-carboxylic acid to cause a preferentially advantageous effect on plants.

The compositions provided herein can further include one or more agriculturally acceptable adjuvant or carrier. Suitable adjuvants or carriers should not be phytotoxic to the *Brassica* species, particularly at the concentrations employed in applying the compositions for selective weed control in the presence of the *Brassica* species and should not react chemically with herbicidal components or other composition ingredients. Such mixtures can be designed for application directly to weeds or their locus or can be concentrates or formulations that are normally diluted with additional carriers and adjuvants before application. The adjuvants or carriers can be solids, such as, for example, dusts, granules, water-dispersible granules, or wettable powders, or liquids, such as, for example, emulsifiable concentrates, solutions, emulsions or suspensions. Additionally, the adjuvants or carriers can also be provided as a pre-mix or tank mixed.

Suitable agricultural adjuvants and carriers are well known to those of skill in the art and include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Examples of liquid carriers that can be used in the compositions and methods described herein include water and organic solvents. Examples of useful organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, dibutyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is useful as a carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

The compositions described herein may further include one or more surface-active agents. Such surface-active agents can be used in both solid and liquid compositions, and can be designed to be diluted with a carrier before application. The surface-active agents can be anionic, cationic or nonionic in character and can be employed as emulsifying agents, wetting agents, suspending agents, or for other purposes. Surfactants which may also be used in the present formulations are described, inter alia, in *McCutcheon's Detergents and Emulsifiers Annual*, MC Publishing Corporation: Ridgewood, N.J., 1998 and in *Encyclopedia of Surfactants*, Vol. I-III, Chemical Publishing Company: New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, e.g., methyl esters. These materials, such as vegetable or seed oils and their esters, can be used interchangeably as an agricultural adjuvant, as a liquid carrier or as a surface active agent.

Other additives useful in the compositions provided herein include, but are not limited to, compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of active ingredients in the compositions described herein is generally from 0.0005 to 98 percent by weight. Additionally, concentrations from 0.0006 to 90 percent by weight can be used. In compositions designed to be employed as concentrates, the active ingredients can be present in a concentration from 0.1 to 98 weight percent or from 0.5 to 90 weight percent. Such compositions can be diluted with an inert carrier, such as, for example, water, before application. The diluted compositions usually applied to vegetation or the soil adjacent thereto can contain from 0.0006 to 15.0 weight percent active ingredient or from 0.001 to 10.0 weight percent active ingredient.

III. Methods of Use

Provided herein also are methods for safening *Brassica* species susceptible to injury from 4-amino-3-chloro-6-(4-chloro-2-fluoro-3-methoxyphenyl)-5-fluoropyridine-2-carboxylic acid, including applying to the *Brassica* species, contacting the vegetation, or area adjacent thereto with a herbicidal composition as described herein above. These compositions contain (a) a herbicidally effective amount of 4-amino-3-chloro-6-(4-chloro-2-fluoro-3-methoxyphenyl)-5-fluoropyridine-2-carboxylic acid, an agriculturally acceptable salt or ester thereof, or combinations thereof and (b) a safener. The safener includes one or more herbicides capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species or herbicide safeners capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species or mixtures thereof.

The compositions described herein can be applied either separately or together as part of a system. When part of a system, for example, the 4-amino-3-chloro-6-(4-chloro-2-fluoro-3-methoxyphenyl)-5-fluoropyridine-2-carboxylic acid or an agriculturally acceptable salt or ester of thereof and the one or more herbicides capable of safening or herbicide safeners can be formulated in one composition, tank mixed, applied simultaneously, or applied sequentially. The 4-amino-3-chloro-6-(4-chloro-2-fluoro-3-methoxyphenyl)-5-fluoropyridine-2-carboxylic acid or an agriculturally acceptable salt or ester of thereof and the one or more herbicides capable of safening or herbicide safeners as described herein, can be applied pre-emergently to the *Brassica* species or the undesirable vegetation or post-emergently to the *Brassica* species or the undesirable vegetation.

Herbicidal activity is exhibited by the 4-amino-3-chloro-6-(4-chloro-2-fluoro-3-methoxyphenyl)-5-fluoropyridine-2-carboxylic acid or an agriculturally acceptable salt or ester of thereof, when it is applied directly to a plant or to the area adjacent to the plant at any stage of growth. The herbicidal activity observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. The compositions of 4-amino-3-chloro-6-(4-chloro-2-fluoro-3-methoxyphenyl)-5-fluoropyridine-2-carboxylic acid described herein may be applied as a post-emergence application, or pre-emergence application, to relatively immature undesirable vegetation to achieve the maximum control of the undesirable vegetation.

The application rate will depend upon the particular type of weed to be controlled, the degree of control required, and the timing and method of application. In the compositions described herein the 4-amino-3-chloro-6-(4-chloro-2-fluoro-3-methoxyphenyl)-5-fluoropyridine-2-carboxylic acid, or a salt or ester thereof, can be applied at an application rate of from 1 gram acid equivalent per hectare (g ae/ha) to 25 g ae/ha based on the total amount of the 4-amino-3-chloro-6-(4-chloro-2-fluoro-3-methoxyphenyl)-5-fluoropyridine-2-carboxylic acid, or a salt or ester thereof, in the composition. Additionally, in the compositions described herein the 4-amino-3-chloro-6-(4-chloro-2-fluoro-3-methoxyphenyl)-5-fluoropyridine-2-carboxylic acid, or a salt or ester thereof, can be applied at an application rate of from 1 g ae/ha to 22 g ae/ha, 1 g ae/ha to 20 g ae/ha, 1 g ae/ha to 18 g ae/ha, 1 g ae/ha to 15 g ae/ha, 1 g ae/ha to 12 g ae/ha, 1 g ae/ha to 10 g ae/ha, 1.1 g ae/ha to 25 g ae/ha, 1.1 g ae/ha to 22 g ae/ha, 1.1 g ae/ha to 20 g ae/ha, 1.1 g ae/ha to 18 g ae/ha, 1.1 g ae/ha to 15 g ae/ha, 1.1 g ae/ha to 12 g ae/ha, 1.1 g ae/ha to 10 g ae/ha, 1.25 g ae/ha to 25 g ae/ha, 1.25 g ae/ha to 22 g ae/ha, 1.25 g ae/ha to 20 g ae/ha, 1.25 g ae/ha to 18 g ae/ha, 1.25 g ae/ha to 15 g ae/ha, 1.25 g ae/ha to 12 g ae/ha, 1.15 g ae/ha to 10 g ae/ha, 2.5 g ae/ha to 25 g ae/ha, 2.5 g ae/ha to 20 g ae/ha, 2.5 g ae/ha to 15 g ae/ha, or 2.5 g ae/ha to 10 g ae/ha based on the total amount of the 4-amino-3-chloro-6-(4-chloro-2-fluoro-3-methoxyphenyl)-5-fluoropyridine-2-carboxylic acid, or a salt or ester thereof, in the composition. In the compositions described herein the herbicides capable of safening the 4-amino-3-chloro-6-(4-chloro-2-fluoro-3-methoxyphenyl)-5-fluoropyridine-2-carboxylic acid, or salt or ester thereof, to the *Brassica* species can be applied at an application rate of from 30 g ae/ha to 300 g ae/ha. Additionally, in the compositions described herein the herbicides, capable of safening the 4-amino-3-chloro-6-(4-chloro-2-fluoro-3-methoxyphenyl)-5-fluoropyridine-2-carboxylic acid, or salt or ester thereof, to the *Brassica* species can be applied at an application rate of from 30 g ae/ha to 280 g ae/ha, 30 g ae/ha to 260 g ae/ha, 30 g ae/ha to 240 g ae/ha, 30 g ae/ha to 220 g ae/ha, 30 g ae/ha to 200 g ae/ha, 30 g ae/ha to 180 g ae/ha, 30 g ae/ha to 160 g ae/ha, 30 g ae/ha to 140 g ae/ha, 30 g ae/ha to 120 g ae/ha, 30 g ae/ha to 100 g ae/ha, 30 g ae/ha to 90 g ae/ha, 30 g ae/ha to 80 g ae/ha, 40 g ae/ha to 300 g ae/ha, 40 g ae/ha to 280 g ae/ha, 40 g ae/ha to 260 g ae/ha, 40 g ae/ha to 240 g ae/ha, 40 g ae/ha to 220 g ae/ha, 40 g ae/ha to 200 g ae/ha, 40 g ae/ha to 180 g ae/ha, 40 g ae/ha to 160 g ae/ha, 40 g ae/ha to 140 g ae/ha, 40 g ae/ha to 120 g ae/ha, 40 g ae/ha to 100 g ae/ha, 40 g ae/ha to 90 g ae/ha, 40 g ae/ha to 80 g ae/ha, 50 g ae/ha to 300 g ae/ha, 50 g ae/ha to 280 g ae/ha, 50 g ae/ha to 260 g ae/ha, 50 g ae/ha to 240 g ae/ha, 50 g ae/ha to 220 g ae/ha, 50 g ae/ha to 190 g ae/ha, 50 g ae/ha to 180 g ae/ha, 50 g ae/ha to 160 g ae/ha, 50 g ae/ha to 140 g ae/ha, 50 g ae/ha to 120 g ae/ha, 50 g ae/ha to 100 g ae/ha, 50 g ae/ha to 90 g ae/ha, 50 g ae/ha to 80 g ae/ha, 50 g ae/ha to 290 g ae/ha, 50 g ae/ha to 270 g ae/ha, 30 g ae/ha to 40 g ae/ha, 40 g ae/ha to 50 g ae/ha, 40 g ae/ha to 250 g ae/ha, 50 g ae/ha to 250 g ae/ha, 60 g ae/ha to 300 g ae/ha, 60 g ae/ha to 280 g ae/ha, 70 g ae/ha to 260 g ae/ha, 80 g ae/ha to 250 g ae/ha, 80 g ae/ha to 230 g ae/ha, 80 g ae/ha to 210 g ae/ha, 80 g ae/ha to 190 g ae/ha, 80 g ae/ha to 170 g ae/ha, 90 g ae/ha to 170 g ae/ha, 100 g ae/ha to 170 g ae/ha, or 50 g ae/ha to 200 g ae/ha, based on the total amount of the herbicides, capable of safening the 4-amino-3-chloro-6-(4-chloro-2-fluoro-3-methoxyphenyl)-5-fluoropyridine-2-carboxylic acid to the *Brassica* species in the composition. In the compositions described herein the herbicide safener capable of safening the 4-amino-3-chloro-6-(4-chloro-2-fluoro-3-methoxyphenyl)-5-fluoropyridine-2-carboxylic acid, or salt or ester thereof, to the *Brassica* species can be applied at an application rate of from 2.5 g ae/ha to 50 g ae/ha. Additionally, in the compositions described herein the herbicide safener capable of safening the 4-amino-3-chloro-6-(4-chloro-2-fluoro-3-methoxyphenyl)-5-fluoropyridine-2-carboxylic acid, or salt or ester thereof, to the *Brassica* species can be applied at an application rate of from 2.5 g ae/ha to 48 g ae/ha, 2.5 g ae/ha to 46 g ae/ha, 2.5 g ae/ha to 44 g ae/ha, 2.5 g ae/ha to 42 g ae/ha, 2.5 g ae/ha to 40 g ae/ha, 4 g ae/ha to 50 g ae/ha, 4 g ae/ha to 48 g ae/ha, 4 g ae/ha to 46 g ae/ha, 4 g ae/ha to 45 g ae/ha, 4 g ae/ha to 44 g ae/ha, 4 g ae/ha to 43 g ae/ha, 4 g ae/ha to 42 g ae/ha, 4 g ae/ha to 41 g ae/ha, 4 g ae/ha to 40 g ae/ha, 5 g ae/ha to 50 g ae/ha, 5 g ae/ha to 48 g ae/ha, 5 g ae/ha to 46 g ae/ha, 5 g ae/ha to 45 g ae/ha, 5 g ae/ha to 44 g ae/ha, 5 g ae/ha to 43 g ae/ha, 5 g ae/ha to 42 g ae/ha, 5 g ae/ha to 41 g ae/ha, or 5 g ae/ha to 40 g ae/ha based on the total amount of the herbicide safener capable of safening the 4-amino-3-chloro-6-(4-chloro-2-fluoro-3-methoxyphenyl)-5-fluoropyridine-2-carboxylic acid to the *Brassica* species in the composition. For example, the herbicides capable of safening the 4-amino-3-chloro-6-(4-chloro-2-fluoro-3-methoxyphenyl)-5-fluoropyridine-2-carboxylic acid, or a salt or ester thereof, to the *Brassica* species may be applied at a rate from 30 g ae/ha to 300 g ae/ha, the herbicide safener, capable of safening the 4-amino-3-chloro-6-(4-chloro-2-fluoro-3-methoxyphenyl)-5-fluoropyridine-2-carboxylic acid, or a salt or ester thereof, to the *Brassica* species may be applied at a rate from 5 g ae/ha to 50 g ae/ha, and the 4-amino-3-chloro-6-(4-chloro-2-fluoro-3-methoxyphenyl)-5-fluoropyridine-2-carboxylic acid, or a salt or ester thereof, may be applied at a rate from 1 g ae/ha to 25 g ae/ha.

The components of the mixtures described herein can be applied either separately or as part of a multipart herbicidal system.

The compositions and methods provided herein can be used to control weeds in *Brassica* species, and also in 5-enolpyruvylshikimate-3-phosphate (EPSP) synthase inhibitor-tolerant (e.g., glyphosate-tolerant), glutamine synthetase inhibitor-tolerant (e.g., glufosinate-tolerant), synthetic auxin-tolerant (e.g., dicamba-tolerant, phenoxy auxin-tolerant, pyridyloxy auxin-tolerant), auxin transport inhibitor-tolerant, acetyl CoA carboxylase (ACCase) inhibitor-tolerant (e.g., aryloxyphenoxypropionate-tolerant), acetolactate synthase (ALS) or acetohydroxy acid synthase (AHAS) inhibitor-tolerant (e.g., imidazolinone-tolerant, sulfonylurea-tolerant, pyrimidinylthiobenzoate-tolerant, triazolopyrimidine-tolerant, and sulfonylaminocarbonyltriazolinone-tolerant), 4-hydroxyphenyl-pyruvate dioxygenase (HPPD) inhibitor-tolerant, phytoene desaturase inhibitor-tolerant, carotenoid biosynthesis inhibitor-tolerant, protoporphyrinogen oxidase (PPO) inhibitor-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, and photosystem II inhibitor-tolerant (e.g., triazine-tolerant and bromoxynil-tolerant) *Brassica* species. The compositions and methods provided herein can be applied to nursery *Brassica* species, pre-plant treatments and post-emergence treatments to *Brassica* species. The compositions and methods may be used in controlling undesirable vegetation in *Brassica* species genetically transformed to express specialized traits. Examples of specialized traits may include agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture). Additional examples include those expressing proteins toxic to invertebrate pests, such as *Bacillus thuringiensis* or other insecticidal toxins, or those with multiple or "stacked" foreign genes expressing insecticidal toxins, herbicide resistance, nutrition-enhancement and/or other beneficial traits, for example, grasses possessing multiple or stacked traits conferring tolerance to multiple chemistries and/or multiple modes of action via single and/or multiple resistance mechanisms.

The 4-amino-3-chloro-6-(4-chloro-2-fluoro-3-methoxyphenyl)-5-fluoropyridine-2-carboxylic acid or a salt or ester thereof and a safener containing one or more herbicides capable of safening the 4-amino-3-chloro-6-(4-chloro-2-fluoro-3-methoxyphenyl)-5-fluoropyridine-2-carboxylic acid, or salt or ester thereof, to the *Brassica* species or herbicide safeners capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species can be used in combination with herbicides that are selective to the *Brassica* species and which complement the spectrum of weeds controlled by the 4-amino-3-chloro-6-(4-chloro-2-fluoro-3-methoxyphenyl)-5-fluoropyridine-2-carboxylic acid. The compositions described herein and the complementary herbicides can be applied at the same time, either as a combination formulation, as a tank mix or sequentially. The compositions and methods may be used in controlling undesirable vegetation in *Brassica* species possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The present compositions can be applied to vegetation or the soil or water adjacent thereto by the use of conventional ground or aerial dusters, sprayers, and granule applicators, by addition to irrigation or paddy water, and by other conventional means known to those skilled in the art.

The following Examples are presented to illustrate various aspects of the compositions and methods described herein and should not be construed as limitations to the claims.

EXAMPLES

Example 1. Greenhouse Trials—Methodology—Evaluation of Postemergence Herbicidal Activity in Crops Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

An aliquot of formulated benzyl 4-amino-3-chloro-6-(4-chloro-2-fluoro-3-methoxyphenyl)-5-fluoropyridine-2-carboxylate (florpyrauxifen-benzyl; 300 grams active ingredient per liter (g ai/L) suspension concentrate (SC)) was placed in a 25 mL glass vial and diluted in a volume of 1.25% (v/v) aqueous Agri-dex crop oil concentrate to obtain a stock solution. If the compound did not dissolve readily, the mixture was warmed and/or sonicated. The concentrated stock solutions were diluted with an aqueous mixture of 1.25% v/v of aqueous Agri-dex crop oil concentrate to provide the appropriate application rates. Compound requirements are based upon a 12 milliliter (mL) application volume at a rate of 187 liters per hectare (L/ha). Stock solutions of the formulated materials were prepared following the same procedure. Spray solutions of the compound mixtures were prepared by adding the stock solutions to the appropriate amount of dilution solution to form a 12 mL spray solution. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. Colby's equation was used to determine the herbicidal effects expected from the mixtures.

Benzyl 4-amino-3-chloro-6-(4-chloro-2-fluoro-3-methoxyphenyl)-5-fluoropyridine-2-carboxylate (florpyrauxifen-benzyl, 300 g ai/L SC) was combined in two-, three-, and four-way mixtures with one or more of the following: clopyralid-olamine (as Lontrel™ 35A Herbicidal Concentrate), quinclorac (as Facet 75DF), isoxadifen-ethyl (100 g/L SC), cloquintocet-mexyl (120 g/L EC) or mefenpyr-diethyl (as mefenpyr-diethyl 15WP). The mixtures were applied to kale/Chinese kale (*Brassica* alboglabra, BRSAG), *Juncea* canola or brown mustard (*Brassica juncea*, BRSJU), rutabaga (*Brassica napus* var. *napobrassica*, BRSNA), all varieties of canola and oilseed rape (*Brassica napus*, BRSNN), Nexera™ canola (*Brassica napus*, BRSNN-NEX), winter oilseed rape (*Brassica napus*, BRSNW), Roundup Ready® canola (*Brassica napus*, RR-BRSNN), and turnip or Polish canola (*Brassica rapa*, BRSRR), and the phytotoxicity of the compositions was measured. The results are summarized in Tables 1-9.

Colby's equation was used to determine the herbicidal effects expected from the mixtures evaluated in the described trials (Colby, S. R. Calculation of the synergistic and antagonistic response of herbicide combinations. *Weeds* 1967, 15, 20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture;

B=observed efficacy of active ingredient B at the same concentration as used in the mixture.

The compositions tested, application rates employed, plant species tested, and results are given in Table 1 through Table 9.

The following abbreviations are used in Tables 1 to 9:

BRSAG=*Brassica alboglabra* (kale/Chinese kale)

BRSJU=*Brassica juncea* (*Juncea* canola or brown mustard)

BRSNA=*Brassica napus* var. *napobrassica* (rutabaga)

BRSNN=*Brassica napus* (all varieties of canola and oilseed rape)

BRSNN-NEX=*Brassica napus* (Nexera™ canola)

BRSNW=*Brassica napus* (winter oilseed rape)

BRSRR=*Brassica rapa* (turnip or Polish canola)

RR-BRSNN=*Brassica napus* (Roundup Ready® canola)

g ai/ha=grams active ingredient per hectare

Obs=observed value of percent (%) injury control rated visually

Exp=expected value of percent (%) injury as calculated by Colby's equation

Δ=difference between Obs and Exp values

TABLE 1

Reduction in % Visual Injury to *Brassica* species from Postemergence Applications of Florpyrauxifen-benzyl + Clopyralid-olamine in Greenhouse Trials.

| Application Rate (g ai/ha) | | BRSAG | | BRSJU | | BRSNA | | BRSNN | |
|---|---|---|---|---|---|---|---|---|---|
| Florpyrauxifen-benzyl | Clopyralid-olamine | Obs | Exp | Obs | Exp | Obs | Exp | Obs | Exp |
| 2.5 | 0 | 5 | — | 7 | — | 4 | — | 7 | — |
| 0 | 50 | 0 | — | 0 | — | 0 | — | 2 | — |
| 0 | 100 | 0 | — | 0 | — | 0 | — | 0 | — |
| 0 | 200 | 0 | — | 0 | — | 0 | — | 0 | — |
| 2.5 | 50 | 0 | 5 | 0 | 7 | 0 | 4 | 3 | 8 |
| 2.5 | 100 | 0 | 5 | 0 | 7 | 0 | 4 | 0 | 7 |
| 2.5 | 200 | 0 | 5 | 0 | 7 | 0 | 4 | 0 | 7 |
| 5 | 0 | 3 | — | 12 | — | 4 | — | 12 | — |
| 0 | 50 | 0 | — | 0 | — | 0 | — | 2 | — |
| 0 | 100 | 0 | — | 0 | — | 0 | — | 0 | — |
| 0 | 200 | 0 | — | 0 | — | 0 | — | 0 | — |
| 5 | 50 | 0 | 3 | 3 | 12 | 5 | 4 | 10 | 13 |
| 5 | 100 | 0 | 3 | 0 | 12 | 0 | 4 | 3 | 12 |
| 5 | 200 | 2 | 3 | 0 | 12 | 0 | 4 | 3 | 12 |
| 10 | 0 | 7 | — | 18 | — | 13 | — | 18 | — |
| 0 | 50 | 0 | — | 0 | — | 0 | — | 2 | — |
| 0 | 100 | 0 | — | 0 | — | 0 | — | 0 | — |
| 0 | 200 | 0 | — | 0 | — | 0 | — | 0 | — |
| 10 | 50 | 3 | 7 | 20 | 18 | 14 | 13 | 23 | 19 |
| 10 | 100 | 0 | 7 | 11 | 18 | 6 | 13 | 15 | 18 |
| 10 | 200 | 0 | 7 | 9 | 18 | 10 | 13 | 15 | 18 |

| Application Rate (g ai/ha) | | BRSNN-NEX | | BRSNW | | BRSRR | | RR-BRSNN | |
|---|---|---|---|---|---|---|---|---|---|
| Florpyrauxifen-benzyl | Clopyralid-olamine | Obs | Exp | Obs | Exp | Obs | Exp | Obs | Exp |
| 2.5 | 0 | 7 | — | 8 | — | 6 | — | 6 | — |
| 0 | 50 | 0 | — | 0 | — | 0 | — | 0 | — |
| 0 | 100 | 0 | — | 0 | — | 0 | — | 0 | — |
| 0 | 200 | 0 | — | 0 | — | 0 | — | 0 | — |
| 2.5 | 50 | 0 | 7 | 0 | 8 | 0 | 6 | 2 | 6 |
| 2.5 | 100 | 0 | 7 | 0 | 8 | 0 | 6 | 0 | 6 |
| 2.5 | 200 | 0 | 7 | 0 | 8 | 0 | 6 | 2 | 6 |
| 5 | 0 | 12 | — | 13 | — | 9 | — | 9 | — |
| 0 | 50 | 0 | — | 0 | — | 0 | — | 0 | — |
| 0 | 100 | 0 | — | 0 | — | 0 | — | 0 | — |
| 0 | 200 | 0 | — | 0 | — | 0 | — | 0 | — |
| 5 | 50 | 0 | 12 | 4 | 13 | 10 | 9 | 5 | 9 |
| 5 | 100 | 0 | 12 | 0 | 13 | 4 | 9 | 2 | 9 |
| 5 | 200 | 0 | 12 | 0 | 13 | 0 | 9 | 0 | 9 |
| 10 | 0 | 19 | — | 18 | — | 14 | — | 19 | — |
| 0 | 50 | 0 | — | 0 | — | 0 | — | 0 | — |
| 0 | 100 | 0 | — | 0 | — | 0 | — | 0 | — |
| 0 | 200 | 0 | — | 0 | — | 0 | — | 0 | — |
| 10 | 50 | 10 | 19 | 10 | 18 | 10 | 14 | 15 | 19 |
| 10 | 100 | 10 | 19 | 10 | 18 | 15 | 14 | 12 | 19 |
| 10 | 200 | 8 | 19 | 5 | 18 | 3 | 14 | 13 | 19 |

TABLE 2

Reduction in % Visual Injury to *Brassica* species from Postemergence Applications of Florpyrauxifen-benzyl + Quinclorac in Greenhouse Trials.

| Application Rate (g ai/ha) | | BRSAG | | BRSJU | | BRSNA | | BRSNN | |
|---|---|---|---|---|---|---|---|---|---|
| Florpyrauxifen-benzyl | Quinclorac | Obs | Exp | Obs | Exp | Obs | Exp | Obs | Exp |
| 2.5 | 0 | 5 | — | 7 | — | 4 | — | 7 | — |
| 0 | 50 | 0 | — | 0 | — | 0 | — | 0 | — |
| 0 | 100 | 0 | — | 0 | — | 0 | — | 0 | — |
| 0 | 200 | 0 | — | 0 | — | 0 | — | 0 | — |

TABLE 2-continued

Reduction in % Visual Injury to *Brassica* species from Postemergence Applications of Florpyrauxifen-benzyl + Quinclorac in Greenhouse Trials.

| 2.5 | 50  | 0 | 5 | 3  | 7  | 0  | 4  | 3  | 7  |
|-----|-----|---|---|----|----|----|----|----|----|
| 2.5 | 100 | 0 | 5 | 0  | 7  | 0  | 4  | 0  | 7  |
| 2.5 | 200 | 0 | 5 | 0  | 7  | 0  | 4  | 5  | 7  |
| 5   | 0   | 3 | — | 12 | —  | 4  | —  | 12 | —  |
| 0   | 50  | 0 | — | 0  | —  | 0  | —  | 0  | —  |
| 0   | 100 | 0 | — | 0  | —  | 0  | —  | 0  | —  |
| 0   | 200 | 0 | — | 0  | —  | 0  | —  | 0  | —  |
| 5   | 50  | 2 | 3 | 0  | 12 | 3  | 4  | 3  | 12 |
| 5   | 100 | 0 | 3 | 3  | 12 | 0  | 4  | 4  | 12 |
| 5   | 200 | 3 | 3 | 0  | 12 | 0  | 4  | 3  | 12 |
| 10  | 0   | 7 | — | 18 | —  | 13 | —  | 18 | —  |
| 0   | 50  | 0 | — | 0  | —  | 0  | —  | 0  | —  |
| 0   | 100 | 0 | — | 0  | —  | 0  | —  | 0  | —  |
| 0   | 200 | 0 | — | 0  | —  | 0  | —  | 0  | —  |
| 10  | 50  | 3 | 7 | 11 | 18 | 5  | 13 | 14 | 18 |
| 10  | 100 | 4 | 7 | 7  | 18 | 6  | 13 | 10 | 18 |
| 10  | 200 | 0 | 7 | 10 | 18 | 5  | 13 | 11 | 18 |

| Application Rate (g ai/ha) | | BRSNN-NEX | | BRSNW | | BRSRR | | RR-BRSNN | |
|---|---|---|---|---|---|---|---|---|---|
| Florpyrauxifen-benzyl | Quinclorac | Obs | Exp | Obs | Exp | Obs | Exp | Obs | Exp |
| 2.5 | 0   | 7  | —  | 8  | —  | 6  | —  | 6  | —  |
| 0   | 50  | 0  | —  | 0  | —  | 0  | —  | 0  | —  |
| 0   | 100 | 0  | —  | 0  | —  | 0  | —  | 0  | —  |
| 0   | 200 | 0  | —  | 0  | —  | 0  | —  | 0  | —  |
| 2.5 | 50  | 0  | 7  | 0  | 8  | 3  | 6  | 0  | 6  |
| 2.5 | 100 | 0  | 7  | 0  | 8  | 0  | 6  | 0  | 6  |
| 2.5 | 200 | 0  | 7  | 0  | 8  | 2  | 6  | 0  | 6  |
| 5   | 0   | 12 | —  | 13 | —  | 9  | —  | 9  | —  |
| 0   | 50  | 0  | —  | 0  | —  | 0  | —  | 0  | —  |
| 0   | 100 | 0  | —  | 0  | —  | 0  | —  | 0  | —  |
| 0   | 200 | 0  | —  | 0  | —  | 0  | —  | 0  | —  |
| 5   | 50  | 0  | 12 | 4  | 13 | 10 | 9  | 9  | 9  |
| 5   | 100 | 0  | 12 | 0  | 13 | 6  | 9  | 5  | 9  |
| 5   | 200 | 0  | 12 | 0  | 13 | 3  | 9  | 3  | 9  |
| 10  | 0   | 19 | —  | 18 | —  | 14 | —  | 19 | —  |
| 0   | 50  | 0  | —  | 0  | —  | 0  | —  | 0  | —  |
| 0   | 100 | 0  | —  | 0  | —  | 0  | —  | 0  | —  |
| 0   | 200 | 0  | —  | 0  | —  | 0  | —  | 0  | —  |
| 10  | 50  | 11 | 19 | 10 | 18 | 9  | 14 | 11 | 19 |
| 10  | 100 | 7  | 19 | 5  | 18 | 5  | 14 | 10 | 19 |
| 10  | 200 | 8  | 19 | 8  | 18 | 10 | 14 | 10 | 19 |

TABLE 3

Reduction in % Visual Injury to *Brassica* species from Postemergence Applications of Florpyrauxifen-benzyl + Isoxadifen-ethyl in Greenhouse Trials.

| Application Rate (g ai/ha) | | BRSAG | | BRSJU | | BRSNA | | BRSNN | |
|---|---|---|---|---|---|---|---|---|---|
| Florpyrauxifen-benzyl | Isoxadifen-ethyl | Obs | Exp | Obs | Exp | Obs | Exp | Obs | Exp |
| 2.5 | 0  | 5  | — | 7  | — | 4  | — | 7  | — |
| 0   | 5  | 0  | — | 0  | — | 0  | — | 0  | — |
| 0   | 10 | 0  | — | 0  | — | 0  | — | 0  | — |
| 0   | 20 | 0  | — | 0  | — | 0  | — | 0  | — |
| 0   | 40 | 0  | — | 0  | — | 0  | — | 0  | — |
| 2.5 | 5  | 9  | 5 | 16 | 7 | 10 | 4 | 9  | 7 |
| 2.5 | 10 | 6  | 5 | 19 | 7 | 10 | 4 | 10 | 7 |
| 2.5 | 20 | 8  | 5 | 23 | 7 | 8  | 4 | 14 | 7 |
| 2.5 | 40 | 3  | 5 | 13 | 7 | 5  | 4 | 11 | 7 |
| 5   | 0  | 3  | — | 12 | — | 4  | — | 12 | — |
| 0   | 5  | 0  | — | 0  | — | 0  | — | 0  | — |
| 0   | 10 | 0  | — | 0  | — | 0  | — | 0  | — |
| 0   | 20 | 0  | — | 0  | — | 0  | — | 0  | — |
| 0   | 40 | 0  | — | 0  | — | 0  | — | 0  | — |
| 5   | 5  | 6  | 3 | 19 | 12 | 7 | 4 | 19 | 12 |

TABLE 3-continued

Reduction in % Visual Injury to *Brassica* species from Postemergence Applications of Florpyrauxifen-benzyl + Isoxadifen-ethyl in Greenhouse Trials.

| | | | | | | | | | |
|---|---|---|---|---|---|---|---|---|---|
| 5 | 10 | 8 | 3 | 20 | 12 | 10 | 4 | 19 | 12 |
| 5 | 20 | 11 | 3 | 14 | 12 | 8 | 4 | 18 | 12 |
| 5 | 40 | 9 | 3 | 21 | 12 | 11 | 4 | 24 | 12 |
| 10 | 0 | 7 | — | 18 | — | 13 | — | 18 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 10 | 5 | 18 | 7 | 24 | 18 | 16 | 13 | 23 | 18 |
| 10 | 10 | 15 | 7 | 25 | 18 | 11 | 13 | 23 | 18 |
| 10 | 20 | 13 | 7 | 28 | 18 | 11 | 13 | 26 | 18 |
| 10 | 40 | 11 | 7 | 29 | 18 | 12 | 13 | 28 | 18 |

| Application Rate (g ai/ha) | | BRSNN-NEX | | BRSNW | | BRSRR | | RR-BRSNN | |
|---|---|---|---|---|---|---|---|---|---|
| Florpyrauxifen-benzyl | Isoxadifen-ethyl | Obs | Exp | Obs | Exp | Obs | Exp | Obs | Exp |
| 2.5 | 0 | 7 | — | 8 | — | 6 | — | 6 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 2.5 | 5 | 17 | 7 | 19 | 8 | 11 | 6 | 15 | 6 |
| 2.5 | 10 | 18 | 7 | 16 | 8 | 7 | 6 | 19 | 6 |
| 2.5 | 20 | 16 | 7 | 18 | 8 | 10 | 6 | 14 | 6 |
| 2.5 | 40 | 13 | 7 | 16 | 8 | 5 | 6 | 16 | 6 |
| 5 | 0 | 12 | — | 13 | — | 9 | — | 9 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 5 | 5 | 30 | 12 | 26 | 13 | 11 | 9 | 23 | 9 |
| 5 | 10 | 34 | 12 | 20 | 13 | 14 | 9 | 23 | 9 |
| 5 | 20 | 31 | 12 | 26 | 13 | 13 | 9 | 28 | 9 |
| 5 | 40 | 30 | 12 | 28 | 13 | 13 | 9 | 32 | 9 |
| 10 | 0 | 19 | — | 18 | — | 14 | — | 19 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 10 | 5 | 35 | 19 | 31 | 18 | 19 | 14 | 26 | 19 |
| 10 | 10 | 38 | 19 | 33 | 18 | 19 | 14 | 28 | 19 |
| 10 | 20 | 36 | 19 | 32 | 18 | 19 | 14 | 31 | 19 |
| 10 | 40 | 39 | 19 | 26 | 18 | 18 | 14 | 31 | 19 |

TABLE 4

Reduction in % Visual Injury to *Brassica* species from Postemergence Applications of Florpyrauxifen-benzyl + Cloquintocet-Mexyl in Greenhouse Trials.

| Application Rate (g ai/ha) | | BRSAG | | BRSJU | | BRSNA | | BRSNN | |
|---|---|---|---|---|---|---|---|---|---|
| Florpyrauxifen-benzyl | Cloquintocet-mexyl | Obs | Exp | Obs | Exp | Obs | Exp | Obs | Exp |
| 2.5 | 0 | 5 | — | 7 | — | 4 | — | 7 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 2.5 | 5 | 3 | 5 | 9 | 7 | 5 | 4 | 12 | 7 |
| 2.5 | 10 | 0 | 5 | 8 | 7 | 3 | 4 | 11 | 7 |
| 2.5 | 20 | 1 | 5 | 11 | 7 | 1 | 4 | 9 | 7 |
| 2.5 | 40 | 4 | 5 | 13 | 7 | 1 | 4 | 9 | 7 |
| 5 | 0 | 3 | — | 12 | — | 4 | — | 12 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 5 | 5 | 1 | 3 | 21 | 12 | 4 | 4 | 16 | 12 |
| 5 | 10 | 1 | 3 | 10 | 12 | 3 | 4 | 19 | 12 |

TABLE 4-continued

Reduction in % Visual Injury to *Brassica* species from Postemergence Applications of Florpyrauxifen-benzyl + Cloquintocet-Mexyl in Greenhouse Trials.

| 5 | 20 | 3 | 3 | 9 | 12 | 4 | 4 | 16 | 12 |
|---|---|---|---|---|---|---|---|---|---|
| 5 | 40 | 3 | 3 | 14 | 12 | 0 | 4 | 18 | 12 |
| 10 | 0 | 7 | — | 18 | — | 13 | — | 18 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 10 | 5 | 3 | 7 | 17 | 18 | 3 | 13 | 16 | 18 |
| 10 | 10 | 4 | 7 | 15 | 18 | 4 | 13 | 14 | 18 |
| 10 | 20 | 0 | 7 | 16 | 18 | 5 | 13 | 12 | 18 |
| 10 | 40 | 3 | 7 | 12 | 18 | 3 | 13 | 16 | 18 |

| Application Rate (g ai/ha) | | BRSNN-NEX | | BRSNW | | BRSRR | | RR-BRSNN | |
|---|---|---|---|---|---|---|---|---|---|
| Florpyrauxifen-benzyl | Cloquintocet-mexyl | Obs | Exp | Obs | Exp | Obs | Exp | Obs | Exp |
| 2.5 | 0 | 7 | — | 8 | — | 6 | — | 6 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 2.5 | 5 | 11 | 7 | 14 | 8 | 11 | 6 | 9 | 6 |
| 2.5 | 10 | 8 | 7 | 10 | 8 | 13 | 6 | 6 | 6 |
| 2.5 | 20 | 6 | 7 | 8 | 8 | 12 | 6 | 6 | 6 |
| 2.5 | 40 | 9 | 7 | 10 | 8 | 13 | 6 | 13 | 6 |
| 5 | 0 | 12 | — | 13 | — | 9 | — | 9 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 5 | 5 | 19 | 12 | 14 | 13 | 11 | 9 | 12 | 9 |
| 5 | 10 | 18 | 12 | 16 | 13 | 12 | 9 | 14 | 9 |
| 5 | 20 | 16 | 12 | 19 | 13 | 13 | 9 | 17 | 9 |
| 5 | 40 | 18 | 12 | 14 | 13 | 9 | 9 | 18 | 9 |
| 10 | 0 | 19 | — | 18 | — | 14 | — | 19 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 10 | 5 | 27 | 19 | 24 | 18 | 9 | 14 | 8 | 19 |
| 10 | 10 | 28 | 19 | 22 | 18 | 13 | 14 | 11 | 19 |
| 10 | 20 | 32 | 19 | 25 | 18 | 9 | 14 | 14 | 19 |
| 10 | 40 | 30 | 19 | 16 | 18 | 12 | 14 | 15 | 19 |

TABLE 5

Reduction in % Visual Injury to *Brassica* species from Postemergence Applications of Florpyrauxifen-benzyl + Mefenpyr-Diethyl in Greenhouse Trials.

| Application Rate (g ai/ha) | | BRSAG | | BRSJU | | BRSNA | | BRSNN | |
|---|---|---|---|---|---|---|---|---|---|
| Florpyrauxifen-benzyl | Mefenpyr-diethyl | Obs | Exp | Obs | Exp | Obs | Exp | Obs | Exp |
| 2.5 | 0 | 5 | — | 7 | — | 4 | — | 7 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 2.5 | 5 | 1 | 5 | 12 | 7 | 0 | 4 | 13 | 7 |
| 2.5 | 10 | 0 | 5 | 5 | 7 | 0 | 4 | 15 | 7 |
| 2.5 | 20 | 0 | 5 | 9 | 7 | 1 | 4 | 12 | 7 |
| 2.5 | 40 | 3 | 5 | 9 | 7 | 4 | 4 | 18 | 7 |
| 5 | 0 | 3 | — | 12 | — | 4 | — | 12 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 5 | 5 | 8 | 3 | 19 | 12 | 4 | 4 | 16 | 12 |

TABLE 5-continued

Reduction in % Visual Injury to *Brassica* species from Postemergence Applications of Florpyrauxifen-benzyl + Mefenpyr-Diethyl in Greenhouse Trials.

| Florpyrauxifen-benzyl | Mefenpyr-diethyl | Obs | Exp | Obs | Exp | Obs | Exp | Obs | Exp |
|---|---|---|---|---|---|---|---|---|---|
| 5 | 10 | 3 | 3 | 15 | 12 | 4 | 4 | 16 | 12 |
| 5 | 20 | 3 | 3 | 16 | 12 | 5 | 4 | 14 | 12 |
| 5 | 40 | 3 | 3 | 14 | 12 | 5 | 4 | 16 | 12 |
| 10 | 0 | 7 | — | 18 | — | 13 | — | 18 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 10 | 5 | 0 | 7 | 21 | 18 | 0 | 13 | 21 | 18 |
| 10 | 10 | 0 | 7 | 20 | 18 | 0 | 13 | 19 | 18 |
| 10 | 20 | 0 | 7 | 19 | 18 | 3 | 13 | 19 | 18 |
| 10 | 40 | 5 | 7 | 21 | 18 | 3 | 13 | 18 | 18 |

| Application Rate (g ai/ha) | | BRSNN-NEX | | BRSNW | | BRSRR | | RR-BRSNN | |
|---|---|---|---|---|---|---|---|---|---|
| Florpyrauxifen-benzyl | Mefenpyr-diethyl | Obs | Exp | Obs | Exp | Obs | Exp | Obs | Exp |
| 2.5 | 0 | 7 | — | 8 | — | 6 | — | 6 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 2.5 | 5 | 14 | 7 | 17 | 8 | 13 | 6 | 8 | 6 |
| 2.5 | 10 | 13 | 7 | 18 | 8 | 6 | 6 | 10 | 6 |
| 2.5 | 20 | 11 | 7 | 11 | 8 | 10 | 6 | 6 | 6 |
| 2.5 | 40 | 12 | 7 | 22 | 8 | 15 | 6 | 8 | 6 |
| 5 | 0 | 12 | — | 13 | — | 9 | — | 9 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 2.5 | 0 | 7 | — | 8 | — | 6 | — | 6 | — |
| 5 | 5 | 27 | 12 | 21 | 13 | 17 | 9 | 18 | 9 |
| 5 | 10 | 22 | 12 | 20 | 13 | 14 | 9 | 13 | 9 |
| 5 | 20 | 20 | 12 | 24 | 13 | 16 | 9 | 11 | 9 |
| 5 | 40 | 18 | 12 | 23 | 13 | 18 | 9 | 15 | 9 |
| 10 | 0 | 19 | — | 18 | — | 14 | — | 19 | — |
| 0 | 5 | 0 | — | 0 | — | 0 | — | 0 | — |
| 0 | 10 | 0 | — | 0 | — | 0 | — | 0 | — |
| 0 | 20 | 0 | — | 0 | — | 0 | — | 0 | — |
| 0 | 40 | 0 | — | 0 | — | 0 | — | 0 | — |
| 10 | 5 | 25 | 19 | 26 | 18 | 9 | 14 | 16 | 19 |
| 10 | 10 | 27 | 19 | 25 | 18 | 8 | 14 | 15 | 19 |
| 10 | 20 | 23 | 19 | 26 | 18 | 8 | 14 | 17 | 19 |
| 10 | 40 | 21 | 19 | 22 | 18 | 9 | 14 | 13 | 19 |

TABLE 6

Reduction in % Visual Injury to *Brassica* species from Postemergence Applications of Florpyrauxifen-benzyl + Clopyralid-olamine + Isoxadifen-ethyl in Greenhouse Trials.

| Application Rate (g ai/ha) | | | BRSAG | | BRSJU | | BRSNA | | BRSNN | |
|---|---|---|---|---|---|---|---|---|---|---|
| Florpyrauxifen-benzyl | Clopyralid-olamine | Isoxadifen-ethyl | Obs | Exp | Obs | Exp | Obs | Exp | Obs | Exp |
| 2.5 | 0 | 0 | 5 | — | 7 | — | 4 | — | 7 | — |
| 5 | 0 | 0 | 3 | — | 12 | — | 4 | — | 12 | — |
| 10 | 0 | 0 | 7 | — | 18 | — | 13 | — | 18 | — |
| 0 | 50 | 0 | 0 | — | 0 | — | 0 | — | 2 | — |
| 0 | 100 | 0 | 0 | — | 0 | — | 0 | — | 0 | — |
| 0 | 200 | 0 | 0 | — | 0 | — | 0 | — | 0 | — |
| 0 | 0 | 5 | 0 | — | 0 | — | 0 | — | 0 | — |
| 0 | 0 | 10 | 0 | — | 0 | — | 0 | — | 0 | — |
| 0 | 0 | 20 | 0 | — | 0 | — | 0 | — | 0 | — |
| 0 | 0 | 40 | 0 | — | 0 | — | 0 | — | 0 | — |
| 2.5 | 50 | 5 | 0 | 5 | 6 | 7 | 0 | 4 | 6 | 7 |
| 2.5 | 50 | 10 | 0 | 5 | 4 | 7 | 0 | 4 | 3 | 7 |
| 2.5 | 50 | 20 | 0 | 5 | 0 | 7 | 0 | 4 | 6 | 7 |
| 2.5 | 50 | 40 | 0 | 5 | 3 | 7 | 2 | 4 | 0 | 7 |

TABLE 6-continued

Reduction in % Visual Injury to *Brassica* species from Postemergence Applications of Florpyrauxifen-benzyl + Clopyralid-olamine + Isoxadifen-ethyl in Greenhouse Trials.

| 2.5 | 100 | 5 | 0 | 5 | 4 | 7 | 0 | 4 | 2 | 7 |
|---|---|---|---|---|---|---|---|---|---|---|
| 2.5 | 100 | 10 | 0 | 5 | 0 | 7 | 2 | 4 | 0 | 7 |
| 2.5 | 100 | 20 | 0 | 5 | 3 | 7 | 0 | 4 | 4 | 7 |
| 2.5 | 100 | 40 | 0 | 5 | 3 | 7 | 3 | 4 | 6 | 7 |
| 2.5 | 200 | 5 | 0 | 5 | 2 | 7 | 2 | 4 | 2 | 7 |
| 2.5 | 200 | 10 | 0 | 5 | 4 | 7 | 0 | 4 | 4 | 7 |
| 2.5 | 200 | 20 | 0 | 5 | 0 | 7 | 0 | 4 | 6 | 7 |
| 2.5 | 200 | 40 | 0 | 5 | 0 | 7 | 0 | 4 | 3 | 7 |
| 5 | 50 | 5 | 0 | 3 | 11 | 12 | 5 | 4 | 6 | 12 |
| 5 | 50 | 10 | 0 | 3 | 10 | 12 | 5 | 4 | 9 | 12 |
| 5 | 50 | 20 | 0 | 3 | 18 | 12 | 0 | 4 | 11 | 12 |
| 5 | 50 | 40 | 0 | 3 | 0 | 12 | 2 | 4 | 10 | 12 |
| 5 | 100 | 5 | 0 | 3 | 4 | 12 | 0 | 4 | 6 | 12 |
| 5 | 100 | 10 | 0 | 3 | 0 | 12 | 0 | 4 | 5 | 12 |
| 5 | 100 | 20 | 0 | 3 | 4 | 12 | 0 | 4 | 8 | 12 |
| 5 | 100 | 40 | 4 | 3 | 10 | 12 | 5 | 4 | 5 | 12 |
| 5 | 200 | 5 | 2 | 3 | 9 | 12 | 0 | 4 | 3 | 12 |
| 5 | 200 | 10 | 0 | 3 | 4 | 12 | 3 | 4 | 2 | 12 |
| 5 | 200 | 20 | 3 | 3 | 8 | 12 | 4 | 4 | 3 | 12 |
| 5 | 200 | 40 | 4 | 3 | 4 | 12 | 3 | 4 | 9 | 12 |
| 10 | 50 | 5 | 8 | 7 | 6 | 18 | 6 | 13 | 11 | 18 |
| 10 | 50 | 10 | 5 | 7 | 14 | 18 | 8 | 13 | 10 | 18 |
| 10 | 50 | 20 | 5 | 7 | 8 | 18 | 5 | 13 | 13 | 18 |
| 10 | 50 | 40 | 5 | 7 | 6 | 18 | 6 | 13 | 13 | 18 |
| 10 | 100 | 5 | 0 | 7 | 16 | 18 | 3 | 13 | 15 | 18 |
| 10 | 100 | 10 | 0 | 7 | 15 | 18 | 4 | 13 | 14 | 18 |
| 10 | 100 | 20 | 0 | 7 | 16 | 18 | 5 | 13 | 12 | 18 |
| 10 | 100 | 40 | 0 | 7 | 14 | 18 | 5 | 13 | 13 | 18 |
| 10 | 200 | 5 | 0 | 7 | 3 | 18 | 5 | 13 | 12 | 18 |
| 10 | 200 | 10 | 0 | 7 | 4 | 18 | 4 | 13 | 8 | 18 |
| 10 | 200 | 20 | 0 | 7 | 5 | 18 | 3 | 13 | 9 | 18 |
| 10 | 200 | 40 | 0 | 7 | 5 | 18 | 4 | 13 | 10 | 18 |

| Application Rate (g ai/ha) | | | BRSNN-NEX | | BRSNW | | BRSRR | | RR-BRSNN | |
|---|---|---|---|---|---|---|---|---|---|---|
| Florpyrauxifen-benzyl | Clopyralid-olamine | Isoxadifen-ethyl | Obs | Exp | Obs | Exp | Obs | Exp | Obs | Exp |
| 2.5 | 0 | 0 | 7 | — | 8 | — | 6 | — | 6 | — |
| 5 | 0 | 0 | 12 | — | 13 | — | 9 | — | 9 | — |
| 10 | 0 | 0 | 19 | — | 18 | — | 14 | — | 19 | — |
| 0 | 50 | 0 | 0 | — | 0 | — | 0 | — | 0 | — |
| 0 | 100 | 0 | 0 | — | 0 | — | 0 | — | 0 | — |
| 0 | 200 | 0 | 0 | — | 0 | — | 0 | — | 0 | — |
| 0 | 0 | 5 | 0 | — | 0 | — | 0 | — | 0 | — |
| 0 | 0 | 10 | 0 | — | 0 | — | 0 | — | 0 | — |
| 0 | 0 | 20 | 0 | — | 0 | — | 0 | — | 0 | — |
| 0 | 0 | 40 | 0 | — | 0 | — | 0 | — | 0 | — |
| 2.5 | 50 | 5 | 8 | 7 | 9 | 8 | 4 | 6 | 8 | 6 |
| 2.5 | 50 | 10 | 6 | 7 | 6 | 8 | 3 | 6 | 3 | 6 |
| 2.5 | 50 | 20 | 7 | 7 | 4 | 8 | 0 | 6 | 4 | 6 |
| 2.5 | 50 | 40 | 5 | 7 | 5 | 8 | 4 | 6 | 4 | 6 |
| 2.5 | 100 | 5 | 4 | 7 | 4 | 8 | 2 | 6 | 4 | 6 |
| 2.5 | 100 | 10 | 4 | 7 | 4 | 8 | 3 | 6 | 4 | 6 |
| 2.5 | 100 | 20 | 5 | 7 | 5 | 8 | 0 | 6 | 3 | 6 |
| 2.5 | 100 | 40 | 3 | 7 | 3 | 8 | 2 | 6 | 5 | 6 |
| 2.5 | 200 | 5 | 4 | 7 | 4 | 8 | 3 | 6 | 8 | 6 |
| 2.5 | 200 | 10 | 8 | 7 | 4 | 8 | 3 | 6 | 6 | 6 |
| 2.5 | 200 | 20 | 9 | 7 | 5 | 8 | 3 | 6 | 9 | 6 |
| 2.5 | 200 | 40 | 5 | 7 | 4 | 8 | 3 | 6 | 5 | 6 |
| 5 | 50 | 5 | 9 | 12 | 13 | 13 | 3 | 9 | 10 | 9 |
| 5 | 50 | 10 | 6 | 12 | 14 | 13 | 5 | 9 | 10 | 9 |
| 5 | 50 | 20 | 9 | 12 | 10 | 13 | 4 | 9 | 13 | 9 |
| 5 | 50 | 40 | 6 | 12 | 16 | 13 | 5 | 9 | 11 | 9 |
| 5 | 100 | 5 | 0 | 12 | 13 | 13 | 0 | 9 | 7 | 9 |
| 5 | 100 | 10 | 5 | 12 | 10 | 13 | 2 | 9 | 9 | 9 |
| 5 | 100 | 20 | 4 | 12 | 8 | 13 | 2 | 9 | 10 | 9 |
| 5 | 100 | 40 | 11 | 12 | 5 | 13 | 8 | 9 | 7 | 9 |
| 5 | 200 | 5 | 6 | 12 | 4 | 13 | 8 | 9 | 6 | 9 |
| 5 | 200 | 10 | 4 | 12 | 4 | 13 | 5 | 9 | 6 | 9 |
| 5 | 200 | 20 | 7 | 12 | 5 | 13 | 7 | 9 | 6 | 9 |
| 5 | 200 | 40 | 11 | 12 | 4 | 13 | 6 | 9 | 19 | 9 |
| 10 | 50 | 5 | 16 | 19 | 13 | 18 | 9 | 14 | 15 | 19 |
| 10 | 50 | 10 | 16 | 19 | 15 | 18 | 14 | 14 | 18 | 19 |
| 10 | 50 | 20 | 15 | 19 | 15 | 18 | 13 | 14 | 15 | 19 |
| 10 | 50 | 40 | 16 | 19 | 20 | 18 | 10 | 14 | 23 | 19 |

TABLE 6-continued

Reduction in % Visual Injury to *Brassica* species from Postemergence Applications of Florpyrauxifen-benzyl + Clopyralid-olamine + Isoxadifen-ethyl in Greenhouse Trials.

| 10 | 100 | 5  | 19 | 19 | 16 | 18 | 14 | 14 | 11 | 19 |
|----|-----|----|----|----|----|----|----|----|----|----|
| 10 | 100 | 10 | 18 | 19 | 16 | 18 | 13 | 14 | 14 | 19 |
| 10 | 100 | 20 | 18 | 19 | 14 | 18 | 14 | 14 | 18 | 19 |
| 10 | 100 | 40 | 24 | 19 | 11 | 18 | 15 | 14 | 21 | 19 |
| 10 | 200 | 5  | 13 | 19 | 11 | 18 | 10 | 14 | 14 | 19 |
| 10 | 200 | 10 | 11 | 19 | 9  | 18 | 11 | 14 | 15 | 19 |
| 10 | 200 | 20 | 11 | 19 | 11 | 18 | 10 | 14 | 15 | 19 |
| 10 | 200 | 40 | 14 | 19 | 15 | 18 | 10 | 14 | 16 | 19 |

TABLE 7

Reduction in % Visual Injury to *Brassica* species from Postemergence Applications of Florpyrauxifen-benzyl + Quinclorac + Isoxadifen-ethyl in Greenhouse Trials.

| Application Rate (g ai/ha) | | | | | | | | | |
|---|---|---|---|---|---|---|---|---|---|
| Florpyrauxifen-benzyl | Quinclorac | Isoxadifen-ethyl | BRSAG | | BRSJU | | BRSNA | | BRSNN | |
| | | | Obs | Exp | Obs | Exp | Obs | Exp | Obs | Exp |
| 2.5 | 0   | 0  | 5 | —  | 7  | —  | 4  | —  | 7  | —  |
| 5   | 0   | 0  | 3 | —  | 12 | —  | 4  | —  | 12 | —  |
| 10  | 0   | 0  | 7 | —  | 18 | —  | 13 | —  | 18 | —  |
| 0   | 50  | 0  | 0 | —  | 0  | —  | 0  | —  | 0  | —  |
| 0   | 100 | 0  | 0 | —  | 0  | —  | 0  | —  | 0  | —  |
| 0   | 200 | 0  | 0 | —  | 0  | —  | 0  | —  | 0  | —  |
| 0   | 0   | 5  | 0 | —  | 0  | —  | 0  | —  | 0  | —  |
| 0   | 0   | 10 | 0 | —  | 0  | —  | 0  | —  | 0  | —  |
| 0   | 0   | 20 | 0 | —  | 0  | —  | 0  | —  | 0  | —  |
| 0   | 0   | 40 | 0 | —  | 0  | —  | 0  | —  | 0  | —  |
| 2.5 | 50  | 5  | 0 | 5  | 2  | 7  | 0  | 4  | 2  | 7  |
| 2.5 | 50  | 10 | 0 | 5  | 0  | 7  | 0  | 4  | 2  | 7  |
| 2.5 | 50  | 20 | 0 | 5  | 0  | 7  | 0  | 4  | 2  | 7  |
| 2.5 | 50  | 40 | 0 | 5  | 0  | 7  | 0  | 4  | 0  | 7  |
| 2.5 | 100 | 5  | 0 | 5  | 0  | 7  | 0  | 4  | 0  | 7  |
| 2.5 | 100 | 10 | 0 | 5  | 0  | 7  | 0  | 4  | 0  | 7  |
| 2.5 | 100 | 20 | 0 | 5  | 0  | 7  | 0  | 4  | 0  | 7  |
| 2.5 | 100 | 40 | 0 | 5  | 0  | 7  | 0  | 4  | 0  | 7  |
| 2.5 | 200 | 5  | 0 | 5  | 0  | 7  | 0  | 4  | 0  | 7  |
| 2.5 | 200 | 10 | 0 | 5  | 0  | 7  | 0  | 4  | 2  | 7  |
| 2.5 | 200 | 20 | 0 | 5  | 0  | 7  | 2  | 4  | 0  | 7  |
| 2.5 | 200 | 40 | 0 | 5  | 0  | 7  | 0  | 4  | 0  | 7  |
| 5   | 50  | 5  | 0 | 3  | 0  | 12 | 2  | 4  | 3  | 12 |
| 5   | 50  | 10 | 0 | 3  | 3  | 12 | 0  | 4  | 3  | 12 |
| 5   | 50  | 20 | 2 | 3  | 5  | 12 | 0  | 4  | 0  | 12 |
| 5   | 50  | 40 | 0 | 3  | 0  | 12 | 0  | 4  | 0  | 12 |
| 5   | 100 | 5  | 0 | 3  | 0  | 12 | 0  | 4  | 0  | 12 |
| 5   | 100 | 10 | 0 | 3  | 2  | 12 | 2  | 4  | 0  | 12 |
| 5   | 100 | 20 | 0 | 3  | 2  | 12 | 3  | 4  | 0  | 12 |
| 5   | 100 | 40 | 0 | 3  | 0  | 12 | 0  | 4  | 3  | 12 |
| 5   | 200 | 5  | 0 | 3  | 0  | 12 | 0  | 4  | 2  | 12 |
| 5   | 200 | 10 | 0 | 3  | 2  | 12 | 0  | 4  | 3  | 12 |
| 5   | 200 | 20 | 0 | 3  | 0  | 12 | 3  | 4  | 0  | 12 |
| 5   | 200 | 40 | 0 | 3  | 0  | 12 | 0  | 4  | 2  | 12 |
| 10  | 50  | 5  | 0 | 7  | 4  | 18 | 5  | 13 | 4  | 18 |
| 10  | 50  | 10 | 0 | 7  | 0  | 18 | 5  | 13 | 2  | 18 |
| 10  | 50  | 20 | 0 | 7  | 5  | 18 | 4  | 13 | 4  | 18 |
| 10  | 50  | 40 | 0 | 7  | 5  | 18 | 4  | 13 | 3  | 18 |
| 10  | 100 | 5  | 0 | 7  | 6  | 18 | 0  | 13 | 2  | 18 |
| 10  | 100 | 10 | 0 | 7  | 4  | 18 | 0  | 13 | 6  | 18 |
| 10  | 100 | 20 |   | 7  | 3  | 18 | 0  | 13 | 2  | 18 |
| 10  | 100 | 40 | 0 | 7  | 2  | 18 | 0  | 13 | 4  | 18 |
| 10  | 200 | 5  | 0 | 7  | 2  | 18 | 0  | 13 | 3  | 18 |
| 10  | 200 | 10 | 0 | 7  | 0  | 18 | 0  | 13 | 2  | 18 |
| 10  | 200 | 20 | 0 | 7  | 2  | 18 | 2  | 13 | 4  | 18 |
| 10  | 200 | 40 | 0 | 7  | 3  | 18 | 2  | 13 | 3  | 18 |

TABLE 7-continued

Reduction in % Visual Injury to *Brassica* species from Postemergence
Applications of Florpyrauxifen-benzyl + Quinclorac + Isoxadifen-ethyl in Greenhouse Trials.

| Application Rate (g ai/ha) | | | BRSNN-NEX | | BRSNW | | BRSRR | | RR-BRSNN | |
|---|---|---|---|---|---|---|---|---|---|---|
| Florpyrauxifen-benzyl | Quinclorac | Isoxadifen-ethyl | Obs | Exp | Obs | Exp | Obs | Exp | Obs | Exp |
| 2.5 | 0 | 0 | 7 | — | 8 | — | 6 | — | 6 | — |
| 5 | 0 | 0 | 12 | — | 13 | — | 9 | — | 9 | — |
| 10 | 0 | 0 | 19 | — | 18 | — | 14 | — | 19 | — |
| 0 | 50 | 0 | 0 | — | 0 | — | 0 | — | 0 | — |
| 0 | 100 | 0 | 0 | — | 0 | — | 0 | — | 0 | — |
| 0 | 200 | 0 | 0 | — | 0 | — | 0 | — | 0 | — |
| 0 | 0 | 5 | 0 | — | 0 | — | 0 | — | 0 | — |
| 0 | 0 | 10 | 0 | — | 0 | — | 0 | — | 0 | — |
| 0 | 0 | 20 | 0 | — | 0 | — | 0 | — | 0 | — |
| 0 | 0 | 40 | 0 | — | 0 | — | 0 | — | 0 | — |
| 2.5 | 50 | 5 | 2 | 7 | 0 | 8 | 0 | 6 | 4 | 6 |
| 2.5 | 50 | 10 | 0 | 7 | 0 | 8 | 2 | 6 | 5 | 6 |
| 2.5 | 50 | 20 | 0 | 7 | 0 | 8 | 0 | 6 | 0 | 6 |
| 2.5 | 50 | 40 | 2 | 7 | 0 | 8 | 0 | 6 | 3 | 6 |
| 2.5 | 100 | 5 | 0 | 7 | 2 | 8 | 0 | 6 | 2 | 6 |
| 2.5 | 100 | 10 | 0 | 7 | 0 | 8 | 0 | 6 | 0 | 6 |
| 2.5 | 100 | 20 | 2 | 7 | 0 | 8 | 2 | 6 | 5 | 6 |
| 2.5 | 100 | 40 | 0 | 7 | 2 | 8 | 0 | 6 | 2 | 6 |
| 2.5 | 200 | 5 | 2 | 7 | 0 | 8 | 0 | 6 | 2 | 6 |
| 2.5 | 200 | 10 | 2 | 7 | 0 | 8 | 0 | 6 | 2 | 6 |
| 2.5 | 200 | 20 | 0 | 7 | 0 | 8 | 0 | 6 | 2 | 6 |
| 2.5 | 200 | 40 | 0 | 7 | 0 | 8 | 0 | 6 | 0 | 6 |
| 5 | 50 | 5 | 4 | 12 | 4 | 13 | 3 | 9 | 2 | 9 |
| 5 | 50 | 10 | 3 | 12 | 3 | 13 | 4 | 9 | 7 | 9 |
| 5 | 50 | 20 | 3 | 12 | 0 | 13 | 2 | 9 | 6 | 9 |
| 5 | 50 | 40 | 2 | 12 | 0 | 13 | 2 | 9 | 4 | 9 |
| 5 | 100 | 5 | 0 | 12 | 0 | 13 | 0 | 9 | 2 | 9 |
| 5 | 100 | 10 | 2 | 12 | 3 | 13 | 3 | 9 | 3 | 9 |
| 5 | 100 | 20 | 4 | 12 | 3 | 13 | 4 | 9 | 4 | 9 |
| 5 | 100 | 40 | 0 | 12 | 3 | 13 | 3 | 9 | 4 | 9 |
| 5 | 200 | 5 | 0 | 12 | 0 | 13 | 2 | 9 | 2 | 9 |
| 5 | 200 | 10 | 0 | 12 | 0 | 13 | 0 | 9 | 2 | 9 |
| 5 | 200 | 20 | 0 | 12 | 0 | 13 | 0 | 9 | 2 | 9 |
| 5 | 200 | 40 | 6 | 12 | 5 | 13 | 0 | 9 | 4 | 9 |
| 10 | 50 | 5 | 8 | 19 | 4 | 18 | 7 | 14 | 9 | 19 |
| 10 | 50 | 10 | 7 | 19 | 4 | 18 | 4 | 14 | 8 | 19 |
| 10 | 50 | 20 | 4 | 19 | 3 | 18 | 3 | 14 | 7 | 19 |
| 10 | 50 | 40 | 5 | 19 | 5 | 18 | 3 | 14 | 7 | 19 |
| 10 | 100 | 5 | 2 | 19 | 2 | 18 | 4 | 14 | 7 | 19 |
| 10 | 100 | 10 | 2 | 19 | 2 | 18 | 3 | 14 | 9 | 19 |
| 10 | 100 | 20 | 4 | 19 | 0 | 18 | 0 | 14 | 6 | 19 |
| 10 | 100 | 40 | 3 | 19 | 3 | 18 | 3 | 14 | 7 | 19 |
| 10 | 200 | 5 | 3 | 19 | 2 | 18 | 0 | 14 | 4 | 19 |
| 10 | 200 | 10 | 2 | 19 | 0 | 18 | 2 | 14 | 4 | 19 |
| 10 | 200 | 20 | 3 | 19 | 2 | 18 | 2 | 14 | 5 | 19 |
| 10 | 200 | 40 | 4 | 19 | 4 | 18 | 3 | 14 | 6 | 19 |

TABLE 8

Reduction in % Visual Injury to *Brassica* species from Postemergence Applications of
Florpyrauxifen-benzyl + Clopyralid-olamine + Quinclorac in Greenhouse Trials.

| Application Rate (g ai/ha) | | | BRSAG | | BRSJU | | BRSNA | | BRSNN | |
|---|---|---|---|---|---|---|---|---|---|---|
| Florpyrauxifen-benzyl | Clopyralid-olamine | Quinclorac | Obs | Exp | Obs | Exp | Obs | Exp | Obs | Exp |
| 2.5 | 0 | 0 | 5 | — | 7 | — | 4 | — | 7 | — |
| 5 | 0 | 0 | 3 | — | 12 | — | 4 | — | 12 | — |
| 10 | 0 | 0 | 7 | — | 18 | — | 13 | — | 18 | — |
| 0 | 50 | 0 | 0 | — | 0 | — | 0 | — | 2 | — |
| 0 | 100 | 0 | 0 | — | 0 | — | 0 | — | 0 | — |
| 0 | 200 | 0 | 0 | — | 0 | — | 0 | — | 0 | — |
| 0 | 0 | 50 | 0 | — | 0 | — | 0 | — | 0 | — |
| 0 | 0 | 100 | 0 | — | 0 | — | 0 | — | 0 | — |
| 0 | 0 | 200 | 0 | — | 0 | — | 0 | — | 0 | — |
| 2.5 | 50 | 50 | 0 | 5 | 0 | 7 | 0 | 4 | 2 | 7 |

TABLE 8-continued

Reduction in % Visual Injury to *Brassica* species from Postemergence Applications of Florpyrauxifen-benzyl + Clopyralid-olamine + Quinclorac in Greenhouse Trials.

| 2.5 | 50  | 100 | 0 | 5 | 0 | 7  | 0  | 4  | 0  | 7  |
|-----|-----|-----|---|---|---|----|----|----|----|----|
| 2.5 | 50  | 200 | 0 | 5 | 0 | 7  | 0  | 4  | 2  | 7  |
| 2.5 | 100 | 50  | 0 | 5 | 0 | 7  | 0  | 4  | 0  | 7  |
| 2.5 | 100 | 100 | 0 | 5 | 2 | 7  | 0  | 4  | 0  | 7  |
| 2.5 | 100 | 200 | 0 | 5 | 0 | 7  | 0  | 4  | 2  | 7  |
| 2.5 | 200 | 50  | 3 | 5 | 6 | 7  | 0  | 4  | 3  | 7  |
| 2.5 | 200 | 100 | 0 | 5 | 5 | 7  | 0  | 4  | 0  | 7  |
| 2.5 | 200 | 200 | 3 | 5 | 0 | 7  | 0  | 4  | 3  | 7  |
| 5   | 50  | 50  | 3 | 3 | 4 | 12 | 2  | 4  | 2  | 12 |
| 5   | 50  | 100 | 3 | 3 | 2 | 12 | 0  | 4  | 3  | 12 |
| 5   | 50  | 200 | 6 | 3 | 8 | 12 | 5  | 4  | 3  | 12 |
| 5   | 100 | 50  | 5 | 3 | 0 | 12 | 3  | 4  | 2  | 12 |
| 5   | 100 | 100 | 0 | 3 | 5 | 12 | 0  | 4  | 3  | 12 |
| 5   | 100 | 200 | 5 | 3 | 0 | 12 | 0  | 4  | 4  | 12 |
| 5   | 200 | 50  | 3 | 3 | 0 | 12 | 0  | 4  | 2  | 12 |
| 5   | 200 | 100 | 2 | 3 | 5 | 12 | 0  | 4  | 3  | 12 |
| 5   | 200 | 200 | 0 | 3 | 3 | 12 | 0  | 4  | 4  | 12 |
| 10  | 50  | 50  | 0 | 7 | 6 | 18 | 3  | 13 | 8  | 18 |
| 10  | 50  | 100 | 4 | 7 | 8 | 18 | 4  | 13 | 7  | 18 |
| 10  | 50  | 200 | 4 | 7 | 5 | 18 | 11 | 13 | 8  | 18 |
| 10  | 100 | 50  | 4 | 7 | 4 | 18 | 9  | 13 | 13 | 18 |
| 10  | 100 | 100 | 5 | 7 | 7 | 18 | 4  | 13 | 5  | 18 |
| 10  | 100 | 200 | 7 | 7 | 4 | 18 | 6  | 13 | 8  | 18 |
| 10  | 200 | 50  | 4 | 7 | 5 | 18 | 0  | 13 | 10 | 18 |
| 10  | 200 | 100 | 5 | 7 | 4 | 18 | 3  | 13 | 6  | 18 |
| 10  | 200 | 200 | 4 | 7 | 5 | 18 | 6  | 13 | 7  | 18 |

| Application Rate (g ai/ha) | | | BRSNN-NEX | | BRSNW | | BRSRR | | RR-BRSNN | |
|---|---|---|---|---|---|---|---|---|---|---|
| Florpyrauxifen-benzyl | Clopyralid-olamine | Quinclorac | Obs | Exp | Obs | Exp | Obs | Exp | Obs | Exp |
| 2.5 | 0   | 0   | 7  | —  | 8  | —  | 6  | —  | 6  | —  |
| 5   | 0   | 0   | 12 | —  | 13 | —  | 9  | —  | 9  | —  |
| 10  | 0   | 0   | 19 | —  | 18 | —  | 14 | —  | 19 | —  |
| 0   | 50  | 0   | 0  | —  | 0  | —  | 0  | —  | 0  | —  |
| 0   | 100 | 0   | 0  | —  | 0  | —  | 0  | —  | 0  | —  |
| 0   | 200 | 0   | 0  | —  | 0  | —  | 0  | —  | 0  | —  |
| 0   | 0   | 50  | 0  | —  | 0  | —  | 0  | —  | 0  | —  |
| 0   | 0   | 100 | 0  | —  | 0  | —  | 0  | —  | 0  | —  |
| 0   | 0   | 200 | 0  | —  | 0  | —  | 0  | —  | 0  | —  |
| 2.5 | 50  | 50  | 0  | 7  | 0  | 8  | 0  | 6  | 3  | 6  |
| 2.5 | 50  | 100 | 0  | 7  | 0  | 8  | 0  | 6  | 0  | 6  |
| 2.5 | 50  | 200 | 2  | 7  | 0  | 8  | 3  | 6  | 3  | 6  |
| 2.5 | 100 | 50  | 0  | 7  | 0  | 8  | 0  | 6  | 0  | 6  |
| 2.5 | 100 | 100 | 0  | 7  | 0  | 8  | 0  | 6  | 0  | 6  |
| 2.5 | 100 | 200 | 0  | 7  | 0  | 8  | 0  | 6  | 0  | 6  |
| 2.5 | 200 | 50  | 3  | 7  | 0  | 8  | 3  | 6  | 0  | 6  |
| 2.5 | 200 | 100 | 0  | 7  | 0  | 8  | 3  | 6  | 2  | 6  |
| 2.5 | 200 | 200 | 0  | 7  | 0  | 8  | 0  | 6  | 3  | 6  |
| 5   | 50  | 50  | 0  | 12 | 2  | 13 | 0  | 9  | 6  | 9  |
| 5   | 50  | 100 | 0  | 12 | 0  | 13 | 4  | 9  | 6  | 9  |
| 5   | 50  | 200 | 0  | 12 | 4  | 13 | 4  | 9  | 6  | 9  |
| 5   | 100 | 50  | 0  | 12 | 0  | 13 | 0  | 9  | 5  | 9  |
| 5   | 100 | 100 | 4  | 12 | 0  | 13 | 3  | 9  | 4  | 9  |
| 5   | 100 | 200 | 3  | 12 | 2  | 13 | 5  | 9  | 6  | 9  |
| 5   | 200 | 50  | 0  | 12 | 0  | 13 | 4  | 9  | 2  | 9  |
| 5   | 200 | 100 | 0  | 12 | 0  | 13 | 3  | 9  | 3  | 9  |
| 5   | 200 | 200 | 0  | 12 | 0  | 13 | 0  | 9  | 8  | 9  |
| 10  | 50  | 50  | 4  | 19 | 4  | 18 | 5  | 14 | 4  | 19 |
| 10  | 50  | 100 | 3  | 19 | 0  | 18 | 7  | 14 | 10 | 19 |
| 10  | 50  | 200 | 3  | 19 | 0  | 18 | 8  | 14 | 13 | 19 |
| 10  | 100 | 50  | 2  | 19 | 5  | 18 | 9  | 14 | 10 | 19 |
| 10  | 100 | 100 | 3  | 19 | 6  | 18 | 3  | 14 | 9  | 19 |
| 10  | 100 | 200 | 3  | 19 | 5  | 18 | 5  | 14 | 5  | 19 |
| 10  | 200 | 50  | 3  | 19 | 0  | 18 | 4  | 14 | 9  | 19 |
| 10  | 200 | 100 | 0  | 19 | 0  | 18 | 7  | 14 | 6  | 19 |
| 10  | 200 | 200 | 3  | 19 | 3  | 18 | 3  | 14 | 14 | 19 |

TABLE 9

Reduction in % Visual Injury to *Brassica* species from Postemergence Applications of
Florpyrauxifen-benzyl + Clopyralid-olamine + Quinclorac + Isoxadifen-Ethyl in Greenhouse Trials.

| Application Rate (g ai/ha) | | | | BRSAG | | BRSJU | | BRSNA | | BRSNN | |
|---|---|---|---|---|---|---|---|---|---|---|---|
| Florpyrauxifen-benzyl | Clopyralid-olamine | Quinclorac | Isoxadifen-ethyl | Obs | Exp | Obs | Exp | Obs | Exp | Obs | Exp |
| 2.5 | 0 | 0 | 0 | 5 | — | 7 | — | 4 | — | 7 | — |
| 5 | 0 | 0 | 0 | 3 | — | 12 | — | 4 | — | 12 | — |
| 10 | 0 | 0 | 0 | 7 | — | 18 | — | 13 | — | 18 | — |
| 0 | 50 | 0 | 0 | 0 | — | 0 | — | 0 | — | 2 | — |
| 0 | 100 | 0 | 0 | 0 | — | 0 | — | 0 | — | 0 | — |
| 0 | 200 | 0 | 0 | 0 | — | 0 | — | 0 | — | 0 | — |
| 0 | 0 | 50 | 0 | 0 | — | 0 | — | 0 | — | 0 | — |
| 0 | 0 | 100 | 0 | 0 | — | 0 | — | 0 | — | 0 | — |
| 0 | 0 | 200 | 0 | 0 | — | 0 | — | 0 | — | 0 | — |
| 0 | 0 | 0 | 5 | 0 | — | 0 | — | 0 | — | 0 | — |
| 0 | 0 | 0 | 10 | 0 | — | 0 | — | 0 | — | 0 | — |
| 0 | 0 | 0 | 20 | 0 | — | 0 | — | 0 | — | 0 | — |
| 0 | 0 | 0 | 40 | 0 | — | 0 | — | 0 | — | 0 | — |
| 2.5 | 50 | 50 | 5 | 0 | 5 | 0 | 7 | 0 | 4 | 0 | 7 |
| 2.5 | 50 | 50 | 10 | 0 | 5 | 0 | 7 | 0 | 4 | 0 | 7 |
| 2.5 | 50 | 50 | 20 | 0 | 5 | 0 | 7 | 0 | 4 | 0 | 7 |
| 2.5 | 50 | 50 | 40 | 0 | 5 | 0 | 7 | 0 | 4 | 0 | 7 |
| 2.5 | 100 | 100 | 5 | 0 | 5 | 0 | 7 | 0 | 4 | 0 | 7 |
| 2.5 | 100 | 100 | 10 | 0 | 5 | 0 | 7 | 0 | 4 | 0 | 7 |
| 2.5 | 100 | 100 | 20 | 0 | 5 | 0 | 7 | 0 | 4 | 0 | 7 |
| 2.5 | 100 | 100 | 40 | 0 | 5 | 0 | 7 | 0 | 4 | 0 | 7 |
| 2.5 | 200 | 200 | 5 | 0 | 5 | 0 | 7 | 0 | 4 | 0 | 7 |
| 2.5 | 200 | 200 | 10 | 0 | 5 | 0 | 7 | 0 | 4 | 0 | 7 |
| 2.5 | 200 | 200 | 20 | 0 | 5 | 0 | 7 | 0 | 4 | 0 | 7 |
| 2.5 | 200 | 200 | 40 | 0 | 5 | 0 | 7 | 0 | 4 | 0 | 7 |
| 5 | 50 | 50 | 5 | 0 | 3 | 0 | 12 | 0 | 4 | 0 | 12 |
| 5 | 50 | 50 | 10 | 0 | 3 | 0 | 12 | 0 | 4 | 0 | 12 |
| 5 | 50 | 50 | 20 | 0 | 3 | 0 | 12 | 3 | 4 | 0 | 12 |
| 5 | 50 | 50 | 40 | 0 | 3 | 0 | 12 | 0 | 4 | 0 | 12 |
| 5 | 100 | 100 | 5 | 0 | 3 | 0 | 12 | 0 | 4 | 0 | 12 |
| 5 | 100 | 100 | 10 | 0 | 3 | 0 | 12 | 0 | 4 | 0 | 12 |
| 5 | 100 | 100 | 20 | 0 | 3 | 0 | 12 | 0 | 4 | 0 | 12 |
| 5 | 100 | 100 | 40 | 0 | 3 | 0 | 12 | 0 | 4 | 0 | 12 |
| 5 | 200 | 200 | 5 | 0 | 3 | 0 | 12 | 0 | 4 | 0 | 12 |
| 5 | 200 | 200 | 10 | 0 | 3 | 0 | 12 | 0 | 4 | 0 | 12 |
| 5 | 200 | 200 | 20 | 0 | 3 | 0 | 12 | 0 | 4 | 0 | 12 |
| 5 | 200 | 200 | 40 | 0 | 3 | 0 | 12 | 0 | 4 | 0 | 12 |
| 10 | 50 | 50 | 5 | 0 | 7 | 0 | 18 | 3 | 13 | 0 | 18 |
| 10 | 50 | 50 | 10 | 0 | 7 | 0 | 18 | 0 | 13 | 0 | 18 |
| 10 | 50 | 50 | 20 | 0 | 7 | 0 | 18 | 0 | 13 | 0 | 18 |
| 10 | 50 | 50 | 40 | 0 | 7 | 0 | 18 | 0 | 13 | 0 | 18 |
| 10 | 100 | 100 | 5 | 0 | 7 | 0 | 18 | 0 | 13 | 0 | 18 |
| 10 | 100 | 100 | 10 | 0 | 7 | 0 | 18 | 0 | 13 | 0 | 18 |
| 10 | 100 | 100 | 20 | 0 | 7 | 0 | 18 | 0 | 13 | 0 | 18 |
| 10 | 100 | 100 | 40 | 0 | 7 | 0 | 18 | 0 | 13 | 2 | 18 |
| 10 | 200 | 200 | 5 | 0 | 7 | 0 | 18 | 0 | 13 | 0 | 18 |
| 10 | 200 | 200 | 10 | 0 | 7 | 0 | 18 | 0 | 13 | 0 | 18 |
| 10 | 200 | 200 | 20 | 0 | 7 | 0 | 18 | 0 | 13 | 0 | 18 |
| 10 | 200 | 200 | 40 | 0 | 7 | 0 | 18 | 0 | 13 | 0 | 18 |

| Application Rate (g ai/ha) | | | | BRSNN-NEX | | BRSNW | | BRSRR | | RR-BRSNN | |
|---|---|---|---|---|---|---|---|---|---|---|---|
| Florpyrauxifen-benzyl | Clopyralid-olamine | Quinclorac | Isoxadifen-ethyl | Obs | Exp | Obs | Exp | Obs | Exp | Obs | Exp |
| 2.5 | 0 | 0 | 0 | 7 | — | 8 | — | 6 | — | 6 | — |
| 5 | 0 | 0 | 0 | 12 | — | 13 | — | 9 | — | 9 | — |
| 10 | 0 | 0 | 0 | 19 | — | 18 | — | 14 | — | 19 | — |
| 0 | 50 | 0 | 0 | 0 | — | 0 | — | 0 | — | 0 | — |
| 0 | 100 | 0 | 0 | 0 | — | 0 | — | 0 | — | 0 | — |
| 0 | 200 | 0 | 0 | 0 | — | 0 | — | 0 | — | 0 | — |
| 0 | 0 | 50 | 0 | 0 | — | 0 | — | 0 | — | 0 | — |
| 0 | 0 | 100 | 0 | 0 | — | 0 | — | 0 | — | 0 | — |
| 0 | 0 | 200 | 0 | 0 | — | 0 | — | 0 | — | 0 | — |
| 0 | 0 | 0 | 5 | 0 | — | 0 | — | 0 | — | 0 | — |
| 0 | 0 | 0 | 10 | 0 | — | 0 | — | 0 | — | 0 | — |
| 0 | 0 | 0 | 20 | 0 | — | 0 | — | 0 | — | 0 | — |
| 0 | 0 | 0 | 40 | 0 | — | 0 | — | 0 | — | 0 | — |
| 2.5 | 50 | 50 | 5 | 0 | 7 | 0 | 8 | 0 | 6 | 2 | 6 |
| 2.5 | 50 | 50 | 10 | 0 | 7 | 0 | 8 | 0 | 6 | 0 | 6 |

TABLE 9-continued

Reduction in % Visual Injury to *Brassica* species from Postemergence Applications of
Florpyrauxifen-benzyl + Clopyralid-olamine + Quinclorac + Isoxadifen-Ethyl in Greenhouse Trials.

| | | | | | | | | | | | |
|---|---|---|---|---|---|---|---|---|---|---|---|
| 2.5 | 50 | 50 | 20 | 0 | 7 | 0 | 8 | 0 | 6 | 0 | 6 |
| 2.5 | 50 | 50 | 40 | 0 | 7 | 0 | 8 | 0 | 6 | 0 | 6 |
| 2.5 | 100 | 100 | 5 | 0 | 7 | 0 | 8 | 0 | 6 | 0 | 6 |
| 2.5 | 100 | 100 | 10 | 0 | 7 | 0 | 8 | 0 | 6 | 0 | 6 |
| 2.5 | 100 | 100 | 20 | 0 | 7 | 0 | 8 | 0 | 6 | 0 | 6 |
| 2.5 | 100 | 100 | 40 | 0 | 7 | 0 | 8 | 0 | 6 | 0 | 6 |
| 2.5 | 200 | 200 | 5 | 0 | 7 | 0 | 8 | 0 | 6 | 0 | 6 |
| 2.5 | 200 | 200 | 10 | 0 | 7 | 0 | 8 | 0 | 6 | 0 | 6 |
| 2.5 | 200 | 200 | 20 | 0 | 7 | 0 | 8 | 0 | 6 | 0 | 6 |
| 2.5 | 200 | 200 | 40 | 0 | 7 | 0 | 8 | 0 | 6 | 0 | 6 |
| 5 | 50 | 50 | 5 | 0 | 12 | 0 | 13 | 0 | 9 | 0 | 9 |
| 5 | 50 | 50 | 10 | 0 | 12 | 0 | 13 | 0 | 9 | 0 | 9 |
| 5 | 50 | 50 | 20 | 0 | 12 | 0 | 13 | 0 | 9 | 3 | 9 |
| 5 | 50 | 50 | 40 | 0 | 12 | 0 | 13 | 0 | 9 | 0 | 9 |
| 5 | 100 | 100 | 5 | 0 | 12 | 0 | 13 | 0 | 9 | 0 | 9 |
| 5 | 100 | 100 | 10 | 0 | 12 | 0 | 13 | 0 | 9 | 0 | 9 |
| 5 | 100 | 100 | 20 | 0 | 12 | 0 | 13 | 0 | 9 | 0 | 9 |
| 5 | 100 | 100 | 40 | 0 | 12 | 0 | 13 | 0 | 9 | 0 | 9 |
| 5 | 200 | 200 | 5 | 0 | 12 | 0 | 13 | 0 | 9 | 0 | 9 |
| 5 | 200 | 200 | 10 | 0 | 12 | 0 | 13 | 0 | 9 | 0 | 9 |
| 5 | 200 | 200 | 20 | 0 | 12 | 0 | 13 | 0 | 9 | 0 | 9 |
| 5 | 200 | 200 | 40 | 0 | 12 | 0 | 13 | 0 | 9 | 0 | 9 |
| 10 | 50 | 50 | 5 | 2 | 19 | 0 | 18 | 0 | 14 | 3 | 19 |
| 10 | 50 | 50 | 10 | 0 | 19 | 0 | 18 | 0 | 14 | 2 | 19 |
| 10 | 50 | 50 | 20 | 0 | 19 | 0 | 18 | 0 | 14 | 0 | 19 |
| 10 | 50 | 50 | 40 | 2 | 19 | 5 | 18 | 0 | 14 | 2 | 19 |
| 10 | 100 | 100 | 5 | 0 | 19 | 0 | 18 | 0 | 14 | 0 | 19 |
| 10 | 100 | 100 | 10 | 0 | 19 | 0 | 18 | 0 | 14 | 0 | 19 |
| 10 | 100 | 100 | 20 | 0 | 19 | 0 | 18 | 0 | 14 | 0 | 19 |
| 10 | 100 | 100 | 40 | 0 | 19 | 0 | 18 | 0 | 14 | 5 | 19 |
| 10 | 200 | 200 | 5 | 0 | 19 | 0 | 18 | 0 | 14 | 0 | 19 |
| 10 | 200 | 200 | 10 | 0 | 19 | 0 | 18 | 0 | 14 | 0 | 19 |
| 10 | 200 | 200 | 20 | 0 | 19 | 0 | 18 | 0 | 14 | 0 | 19 |
| 10 | 200 | 200 | 40 | 0 | 19 | 0 | 18 | 0 | 14 | 0 | 19 |

The present invention is not limited in scope by the embodiments disclosed herein which are intended as illustrations of a few aspects of the invention and any embodiments which are functionally equivalent are within the scope of this invention. Various modifications of the compositions and methods in addition to those shown and described herein will become apparent to those skilled in the art and are intended to fall within the scope of the appended claims. Further, while only certain representative combinations of the composition components and method steps disclosed herein are specifically discussed in the embodiments above, other combinations of the composition components and method steps will become apparent to those skilled in the art and also are intended to fall within the scope of the appended claims. Thus a combination of components or method steps may be explicitly mentioned herein; however, other combinations of components and method steps are included, even though not explicitly stated. The term comprising and variations thereof as used herein is used synonymously with the term including and variations thereof and are open, non-limiting terms.

What is claimed is:

1. A safened herbicidal composition for use in *Brassica* species susceptible to injury by 4-amino-3-chloro-6-(4-chloro-2-fluoro-3-methoxyphenyl)-5-fluoropyridine-2-carboxylic acid or an agriculturally acceptable salt or ester thereof comprising:
   a) a herbicidally effective amount of 4-amino-3-chloro-6-(4-chloro-2-fluoro-3-methoxyphenyl)-5-fluoropyridine-2-carboxylic acid or an agriculturally acceptable salt or ester thereof; and
   b) a first safener comprising a first herbicide capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species; and
   c) a second safener selected from the group consisting of a second herbicide capable of safening and a herbicide safener, wherein the safened herbicidal composition is capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species; and
   d) optionally, wherein the second safener is a second herbicide, a third safener comprising a herbicide safener, wherein the safened herbicidal composition is capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species.

2. The composition of claim 1, wherein (a) is benzyl 4-amino-3-chloro-6-(4-chloro-2-fluoro-3-methoxyphenyl)-5-fluoropyridine-2-carboxylate.

3. The composition of claim 1, wherein the first herbicide capable of safening is clopyralid, quinclorac, picloram, aminopyralid, or an agriculturally acceptable salt or ester thereof.

4. The composition of claim 1, wherein the first herbicide capable of safening is clopyralid or an agriculturally acceptable salt or ester thereof.

5. The composition of claim 4, wherein the second herbicide capable of safening is quinclorac or an agriculturally acceptable salt or ester thereof.

6. The composition of claim 4, wherein the second safener is isoxadifen.

7. The composition of claim 5, wherein the third safener is isoxadifen.

8. The composition of claim 1, wherein the first herbicide capable of safening is quinclorac or an agriculturally acceptable salt or ester thereof.

9. The composition of claim 8, wherein the second safener is isoxadifen.

10. The composition of claim 1, wherein
   a) the application rate of 4-amino-3-chloro-6-(4-chloro-2-fluoro-3-methoxyphenyl)-5-fluoropyridine-2-carboxylic acid or an agriculturally acceptable salt or ester thereof has a range of 2.5 to 10 g ai/ha; and
   b) the application rate of the first safener has an application range of 50 to 200 g ai/ha; and
   c) the application rate of the second safener has an application range of 5 to 200 g ai/ha.

11. The composition of claim 10, wherein the application rate of the second safener has range of 5 to 40 g ai/ha.

12. The composition of claim 10, wherein the application rate of the second safener has a range of 50 to 200 g ai/ha.

13. The composition of claim 10, wherein the application rate of the third safener has a range of 5 to 40 g ai/ha.

14. The composition of claim 1, further comprising an agriculturally acceptable adjuvant or carrier.

15. The composition of claim 1, wherein the *Brassica* species is 5-enolpyruvylshikimate-3-phosphate (EPSP) synthase inhibitor-tolerant, glutamine synthetase inhibitor-tolerant, synthetic auxin-tolerant, acetyl CoA carboxylase (ACCase) inhibitor-tolerant, acetolactate synthase (ALS) inhibitor-tolerant, 4-hydroxyphenyl-pyruvate dioxygenase (HPPD) inhibitor-tolerant, protoporphyrinogen oxidase (PPO) inhibitor-tolerant, or photosystem II inhibitor-tolerant.

16. The composition of claim 1, wherein the *Brassica* species comprises multiple or stacked traits conferring tolerance to multiple chemistries and/or multiple modes of action.

17. The composition of claim 1, wherein the *Brassica* species susceptible to injury from 4-amino-3-chloro-6-(4-chloro-2-fluoro-3-methoxyphenyl)-5-fluoropyridine-2-carboxylic acid or an agriculturally acceptable salt or ester thereof is Chinese kale (*Brassica alboglabra*, BRSAG), brown mustard (*Brassica juncea*, BRSJU), rutabaga (*Brassica napus* var. *napobrassica*, BRSNA), canola (*Brassica napus*, BRSNN), or turnip (*Brassica rapa*, BRSRR).

18. The composition of claim 17, wherein the *Brassica* species is winter oilseed rape (*Brassica napus*, BRSNW), high omega-9 fatty acid canola (*Brassica napus*, BRSNN-NEX), or glyphosate tolerant canola (*Brassica napus*, RR-BRSNN).

19. A method for safening *Brassica* species susceptible to injury from 4-amino-3-chloro-6-(4-chloro-2-fluoro-3-methoxyphenyl)-5-fluoropyridine-2-carboxylic acid or an agriculturally acceptable salt or ester thereof, comprising applying to the *Brassica* species, and contacting the vegetation, or area adjacent thereto with a herbicidal composition comprising:
   a) a herbicidally effective amount of 4-amino-3-chloro-6-(4-chloro-2-fluoro-3-methoxyphenyl)-5-fluoropyridine-2-carboxylic acid, or an agriculturally acceptable salt or ester thereof; and
   b) a first safener comprising a first herbicide capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species; and
   c) a second safener selected from the group consisting of a second herbicide capable of safening and a herbicide safener, wherein the safened herbicidal composition is capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species; and
   d) optionally, wherein the second safener is a second herbicide, a third safener comprising a herbicide safener, wherein the safened herbicidal composition is capable of safening the 4-amino-3-chloro-6-(4-chloro-2-fluoro-3-methoxyphenyl)-5-fluoropyridine-2-carboxylic acid, or an agriculturally acceptable salt or ester thereof, to the *Brassica* species.

20. The method of 19, wherein (a) is benzyl 4-amino-3-chloro-6-(4-chloro-2-fluoro-3-methoxyphenyl)-5-fluoropyridine-2-carboxylate.

21. The method of claim 19, wherein the first herbicide capable of safening is clopyralid, quinclorac, picloram, aminopyralid, or an agriculturally acceptable salt or ester thereof.

22. The method of claim 19, wherein the first herbicide capable of safening is clopyralid or an agriculturally acceptable salt or ester thereof.

23. The method of claim 22, wherein the second herbicide capable of safening is quinclorac or an agriculturally acceptable salt or ester thereof.

24. The method of claim 22, wherein the second safener is isoxadifen.

25. The method of claim 23, wherein the third safener is isoxadifen.

26. The method of claim 19, wherein the first herbicide capable of safening is quinclorac or an agriculturally acceptable salt or ester thereof.

27. The method of claim 26, wherein the second safener is isoxadifen.

28. The method of claim 19, wherein
   a) the application rate of 4-amino-3-chloro-6-(4-chloro-2-fluoro-3-methoxyphenyl)-5-fluoropyridine-2-carboxylic acid or an agriculturally acceptable salt or ester thereof has a range of 2.5 to 10 g ai/ha; and
   b) the application rate of the first safener has an application range of 50 to 200 g ai/ha; and
   c) the application rate of the second safener has an application range of 5 to 200 g ai/ha.

29. The method of claim 28, wherein the application rate of the second safener has range of 5 to 40 g ai/ha.

30. The method of claim 28, wherein the application rate of the second safener has a range of 50 to 200 g ai/ha.

31. The method of claim 28, wherein the application rate of the third safener has a range of 5 to 40 g ai/ha.

32. The method of claim 19, wherein the safened herbicidal composition further comprises an agriculturally acceptable adjuvant or carrier.

33. The method of claim 19, wherein the (a) and (b) and (c) and optionally (d) are applied pre-emergently to the *Brassica* species or the undesirable vegetation.

34. The method of claim 19, wherein the (a) and (b) and (c) and optionally (d) are applied post-emergently to the *Brassica* species or the undesirable vegetation.

35. The method of claim 19, wherein the *Brassica* species is 5-enolpyruvylshikimate-3-phosphate (EPSP) synthase-tolerant, glutamine synthetase-tolerant, synthetic auxin-tolerant, acetyl CoA carboxylase (ACCase) inhibitor-tolerant, acetolactate synthase (ALS) inhibitor-tolerant, 4-hydroxyphenyl-pyruvate dioxygenase (HPPD) inhibitor-tolerant, protoporphyrinogen oxidase (PPO) inhibitor-tolerant, or photosystem II inhibitor-tolerant.

36. The method of claim 19, wherein the *Brassica* species comprises multiple or stacked traits conferring tolerance to multiple chemistries and/or multiple modes of action.

37. The method of claim 19, wherein the *Brassica* species susceptible to injury from 4-amino-3-chloro-6-(4-chloro-2-fluoro-3-methoxyphenyl)-5-fluoropyridine-2-carboxylic acid or an agriculturally acceptable salt or ester thereof is Chinese kale (*Brassica alboglabra*, BRSAG), brown mustard (*Brassica juncea*, BRSJU), rutabaga (*Brassica napus* var. *napobrassica*, BRSNA), canola (*Brassica napus*, BRSNN), or turnip (*Brassica rapa*, BRSRR).

38. The method of claim 37, wherein the *Brassica* species is winter oilseed rape (*Brassica napus*, BRSNW), high omega-9 fatty acid canola (*Brassica napus*, BRSNN-NEX), or glyphosate tolerant canola (*Brassica napus*, RR-BRSNN).

* * * * *